US011612150B2

(12) United States Patent
Dennis et al.

(10) Patent No.: US 11,612,150 B2
(45) **Date of Patent: *Mar. 28, 2023**

(54) TRANSFERRIN RECEPTOR TRANSGENIC MODELS

(71) Applicant: Denali Therapeutics Inc., South San Francisco, CA (US)

(72) Inventors: Mark S. Dennis, South San Francisco, CA (US); Adam P. Silverman, South San Francisco, CA (US); Joy Yu Zuchero, South San Francisco, CA (US)

(73) Assignee: Denali Therapeutics Inc., South San Francisco, CA (US)

( * ) Notice: Subject to any disclaimer, the term of this patent is extended or adjusted under 35 U.S.C. 154(b) by 880 days.

This patent is subject to a terminal disclaimer.

(21) Appl. No.: 16/165,324

(22) Filed: Oct. 19, 2018

(65) Prior Publication Data

US 2019/0274291 A1 Sep. 12, 2019

Related U.S. Application Data

(63) Continuation of application No. 15/923,928, filed on Mar. 16, 2018, now Pat. No. 10,143,187, which is a continuation of application No. PCT/US2018/018302, filed on Feb. 15, 2018.

(60) Provisional application No. 62/460,692, filed on Feb. 17, 2017, provisional application No. 62/543,658, filed on Aug. 10, 2017, provisional application No. 62/543,559, filed on Aug. 10, 2017, provisional application No. 62/583,314, filed on Nov. 8, 2017.

(51) Int. Cl.

| | |
|---|---|
| ***A01K 67/027*** | (2006.01) |
| ***C07K 14/705*** | (2006.01) |
| ***G01N 33/53*** | (2006.01) |
| ***G01N 33/50*** | (2006.01) |
| ***C07K 14/79*** | (2006.01) |
| ***G01N 33/68*** | (2006.01) |

(52) U.S. Cl.

CPC ...... *A01K 67/0278* (2013.01); *A01K 67/0275* (2013.01); *C07K 14/705* (2013.01); *C07K 14/70582* (2013.01); *C07K 14/79* (2013.01); *G01N 33/5088* (2013.01); *G01N 33/5308* (2013.01); *G01N 33/68* (2013.01); *A01K 2217/00* (2013.01); *A01K 2217/072* (2013.01); *A01K 2217/075* (2013.01); *A01K 2227/105* (2013.01); *A01K 2267/03* (2013.01); *C07K 2319/00* (2013.01); *G01N 2500/10* (2013.01)

(58) Field of Classification Search

None

See application file for complete search history.

(56) References Cited

U.S. PATENT DOCUMENTS

| | | | | |
|---|---|---|---|---|
| 5,254,342 | A | 10/1993 | Shen et al. | |
| 5,527,527 | A | 6/1996 | Friden | |
| 6,743,893 | B2 | 6/2004 | Engler et al. | |
| 7,241,449 | B1 | 7/2007 | Myers et al. | |
| 7,741,446 | B2 | 6/2010 | Pardridge et al. | |
| 7,744,879 | B2 | 6/2010 | Shusta et al. | |
| 8,053,567 | B2 | 11/2011 | Pardridge et al. | |
| 8,084,254 | B2 | 12/2011 | Couraud et al. | |
| 8,293,495 | B2 | 10/2012 | Shusta et al. | |
| 8,417,465 | B2 | 4/2013 | Prabhakarpandian et al. | |
| 8,609,065 | B2 | 12/2013 | Kuik-Romeijn et al. | |
| 8,900,865 | B2 | 12/2014 | Harlow et al. | |
| 9,005,973 | B2 | 4/2015 | Cost et al. | |
| 9,156,889 | B2 | 10/2015 | Nomoto et al. | |
| 9,513,280 | B2 | 12/2016 | Kim et al. | |
| 10,143,187 | B2 | 12/2018 | Dennis et al. | |
| 10,457,717 | B2 | 10/2019 | Chen et al. | |
| 10,759,864 | B2 * | 9/2020 | Sonoda | C07K 16/2806 |
| 11,111,308 | B2 * | 9/2021 | Sonoda | C07K 16/2806 |
| 2003/0074141 | A1 | 4/2003 | Russell | |
| 2005/0170394 | A1 | 8/2005 | Zerangue | |
| 2006/0193776 | A1 | 8/2006 | Goldsmith et al. | |
| 2010/0273200 | A1 | 10/2010 | Niwa et al. | |
| 2013/0318641 | A1 | 11/2013 | Bradley et al. | |
| 2013/0318643 | A1 | 11/2013 | Bradley et al. | |
| 2014/0142370 | A1 | 5/2014 | Wong et al. | |
| 2014/0295547 | A1 | 10/2014 | Kuo et al. | |
| 2015/0044140 | A1 | 2/2015 | Giralt Lledó et al. | |
| 2015/0110791 | A1 | 4/2015 | Zhang et al. | |
| 2015/0196663 | A1 | 7/2015 | Shusta et al. | |
| 2016/0040125 | A1 | 2/2016 | Da Silva Ferreira et al. | |
| 2016/0168253 | A1 | 6/2016 | Bohrmann et al. | |

(Continued)

FOREIGN PATENT DOCUMENTS

| | | | |
|---|---|---|---|
| CN | 1993378 | A | 7/2007 |
| CN | 101410411 | A | 4/2009 |

(Continued)

OTHER PUBLICATIONS

Ji et al. Transgenic Res. 24:227-235, 2015 (Year: 2015).*
Raina et al. Gene 96-100, 2015 (Year: 2015).*
Naito et al. J Reprod Fert 113:137-143, 1998 (Year: 1998).*
Abraham, J. et al., "Structural basis for receptor recognition by New World hemorrhagic fever arenaviruses," Nat. Struct. Mol. Biol., 17(4):438-444, 2010.

(Continued)

*Primary Examiner* — Marcia S Noble
(74) *Attorney, Agent, or Firm* — Kilpatrick Townsend & Stockton LLP

(57) ABSTRACT

In some aspects, the present invention provides chimeric transferrin receptor (TfR) polynucleotides and polypeptides. In other aspects, this invention provides chimeric TfR transgenic animal models and methods of using the animal models to identify therapeutics that can cross the blood-brain barrier.

32 Claims, 7 Drawing Sheets

Specification includes a Sequence Listing.

(56) References Cited

U.S. PATENT DOCUMENTS

| | | | |
|---|---|---|---|
| 2016/0339116 A1 | 11/2016 | Chang et al. | |
| 2017/0191055 A1 | 7/2017 | Short et al. | |
| 2018/0171012 A1* | 6/2018 | Sonoda | C07K 19/00 |
| 2018/0179291 A1* | 6/2018 | Sonoda | A61P 25/00 |
| 2018/0235195 A1 | 8/2018 | Dennis et al. | |
| 2018/0237496 A1 | 8/2018 | Chen et al. | |
| 2019/0338043 A1* | 11/2019 | Sonoda | A61K 39/00 |
| 2020/0262890 A1 | 8/2020 | Chen et al. | |
| 2020/0384061 A1* | 12/2020 | Sonoda | A61P 25/08 |
| 2021/0269543 A1* | 9/2021 | Sonoda | A61K 47/6815 |

FOREIGN PATENT DOCUMENTS

| | | | |
|---|---|---|---|
| CN | 103897033 | A | 7/2014 |
| EP | 2 568 051 | A1 | 3/2013 |
| WO | 1991/005038 | A1 | 4/1991 |
| WO | 1994/028121 | A1 | 12/1994 |
| WO | 1999/000150 | A2 | 1/1999 |
| WO | 2001/059459 | A2 | 8/2001 |
| WO | 2001/064849 | A1 | 9/2001 |
| WO | 2003/003007 | A2 | 1/2003 |
| WO | 2004/094647 | A2 | 11/2004 |
| WO | 2010/014622 | A2 | 2/2010 |
| WO | 2012/075037 | A1 | 6/2012 |
| WO | 2012/143379 | A1 | 10/2012 |
| WO | 2013/091637 | A1 | 6/2013 |
| WO | 2013/177062 | A2 | 11/2013 |
| WO | 2014/033074 | A1 | 3/2014 |
| WO | 2014/074695 | A1 | 5/2014 |
| WO | 2014/189973 | A2 | 11/2014 |
| WO | 2015/014884 | A1 | 2/2015 |
| WO | 2015/101586 | A1 | 7/2015 |
| WO | 2016/038123 | A1 | 3/2016 |
| WO | 2016/077840 | A2 | 5/2016 |
| WO | 2016/081640 | A1 | 5/2016 |
| WO | 2016/081643 | A1 | 5/2016 |
| WO | 2016/090486 | A1 | 6/2016 |
| WO | 2016/202343 | A1 | 12/2016 |
| WO | 2016/207091 | A1 | 12/2016 |
| WO | 2016/207240 | A1 | 12/2016 |
| WO | 2016/208695 | A1 | 12/2016 |
| WO | 2017/035119 | A1 | 3/2017 |
| WO | 2018/152375 | A2 | 8/2018 |

OTHER PUBLICATIONS

Alvarez, E. et al., “Intermolecular disulfide bonds are not required for the expression of the dimeric state and functional activity of the transferrin receptor,” The EMBO Journal, 8(8):2231-2240, 1989.

Atwal, J. et al., “A Therapeutic Antibody Targeting BACE1 Inhibits Amyloid-β Production in Vivo,” Sci Transl. Med. 3:84ra43, 2014.

Banks, W., “Mouse Models of Neurological Disorders: A View From the Blood-brain Barrier,” Biochem Biophys Acta, 1802(10):881-888, 2010.

Buchegger, F. et al., “Functional analysis of human/chicken transferrin receptor chimeras indicates that the carboxy-terminal region is important for ligand binding,” Eur. J. Biochem., 235, 9-17, 1996.

Dominguez, A. et al., “Beyond editing: repurposing CRISPR-Cas9 for precision genome regulation and interrogation,” Nature Rev. Molec Cell. Biol., 17:5-15, 2016.

Denali Therapeutics Inc., Form S-1 Registration Statement, as filed with the U.S. Securities and Exchange Commission on Nov. 13, 2017, retrieved online at <https://www.sec.gov/Archives/edgar/data/1714899/000119312517340997/d445892ds1.htm> on Mar. 20, 2018, 292 pages.

Eckenroth, B. E. et al., “How the binding of human transferrin primes the transferrin receptor potentiating iron release at endosomal pH,” Proceedings of the National Academy of Sciences, 108(32):13089-13094, 2011.

Ji et al., “Efficient Creation of an APOE Knockout Rabbit”, Transgenic Res, vol. 24, 2015, pp. 227-235.

Lawrence, C. et al., “Crystal Structure of the Ectodomain of Human Transferrin Receptor,” Science, 286:779-782, 1999.

Li et al., “Production of Genetically Engineered Golden Syrian Hamsters by Pronuclear Injection of the CRISPR/Cas9 Complex”, J Vis Exp, vol. 131, Jan. 2018, 2 pages.

Ma et al., “Generation of eGFP and Cre knockin rats by CRISPR/Cas9”, FEBS Journal, vol. 281, 2016, pp. 3779-3790.

Mcgraw, T. et al., “Functional Expression of the Human Transferrin Receptor cDNA in Chinese Hamster Ovary Cells Deficient in Endogenous Transferrin Receptor,” J. Cell Biology, 105:207-214, 1987.

Milstone, L. et al., “Stratum-Specific Expression of Human Transferrin Receptor Increases Iron in Mouse Epidermas,” J. Invest. Dermatol, 126:648-652, 2006.

Mizutani, Taketoshi et al., “Transferrin Receptor 1 Facilitates Poliovirus Permeation of Mouse Brain Capillary Endothelial Cells,” Journal Of Biological Chemistry, 291(6): 2829-2836, 2016.

Naito et al., “Expression of Exogenous DNA in the Gonads of Chimaeric Chicken Embryos Produced by Transfer of Primordial Germ Cells Transfected In Vitro and Subsequent Fate of the Introduced DNA”, Journal of Reproduction and Fertility, vol. 113, No. 1, May 1998, pp. 137-143.

Palermo, Laura M. et al., “Residues in the apical domain of the feline and canine transferrin receptors control host-specific binding and cell infection of canine and feline parvoviruses,” Journal of Virology, The American Society for Microbiology, 77(16):8915-8923, 2003.

Pardridge, W.M., “Blood-brain barrier drug delivery of IgG fusion proteins with a transferrin receptor monoclonal antibody,” Expert Opinion on Drug Deli, Informa Healthcare, UK, 12(2):207-222, 2015.

Raina et al., “Testis Mediated Gene Transfer: In Vitro Transfection in Goat Testis by Electroporation”, Gene, vol. 554, Issue 1, Jan. 1, 2015, pp. 96-100.

Ramírez-Solis et al., “Gene Targeting in Embryonic Stem Cells”, Methods in Enzymology, vol. 225, 1993, pp. 855-878.

Sohet, F. and Daneman, R., “Genetic mouse models to study blood-brain barrier development and function,” Fluids and Barriers of the CNS 10:3, 2013.

Wen, J. et al. “Soluble Form of Canine Transferrin Receptor Inhibits Canine Parvovirus Infection In Vitro and In Vivo,” BioMed Research Intl., 2013:8, 2013.

Winnard, P. et al., “Development of novel chimeric transmembrane proteins for multimodality imaging of cancer cells,” Cancer Biol. & Ther., 6:12, 1889-1899, 2007.

Yu, Y. Joy et al., “Therapeutic bispecific antibodies cross the blood-brain barrier in nonhuman primates,” Science Translational Medicine, 6(261), 261ra154, 11 pages, 2014.

International Search Report for PCT/US2018/018302, dated May 4, 2018, 6 pages.

Partial International Search Report for PCT/US2018/018445, dated May 9, 2018, 5 pages.

International Search Report for PCT/US2018/018445, dated Aug. 16, 2018, 9 pages.

Helguera et al., “An Antibody Recognizing the Apical Domain of Human Transferrin Receptor 1 Efficiently Inhibits the Entry of All New World Hemorrhagic Fever Arenaviruses”, Journal of Virology, vol. 86, No. 7, 2012, pp. 4024-4028.

Wang et al., “Identification of the Segments of the Mouse Transferrin Receptor 1 Required for Mouse Mammary Tumor Virus Infection”, The Journal of Biological Chemistry, vol. 281, No. 15, 2006, pp. 10243-10249.

* cited by examiner

IV 5 mg/kg anti-TfR

IV 5 mg/kg anti-TfR

IV 50 mg/kg anti-BACE1

IV 50 mg/kg anti-TfR/BACE1

TRANSFERRIN RECEPTOR TRANSGENIC MODELS

CROSS-REFERENCE TO RELATED APPLICATIONS

The present application is a continuation of U.S. patent application Ser. No. 15/923,928, filed Mar. 16, 2018 (Allowed), which is a continuation of International Patent Application Serial No. PCT/US2018/018302, filed Feb. 15, 2018, which application claims the benefit of U.S. Patent Application Ser. No. 62/460,692, filed Feb. 17, 2017, U.S. Patent Application Ser. No. 62/543,658, filed Aug. 10, 2017, U.S. Patent Application Ser. No. 62/543,559, filed Aug. 10, 2017 and U.S. Patent Application Ser. No. 62/583,314, filed Nov. 8, 2017, the contents of which are incorporated herein by reference for all purposes.

BACKGROUND OF THE INVENTION

The blood-brain barrier (BBB) blocks the passage of most macromolecules from the periphery into the brain and thus limits the uses of large molecule therapeutics where brain exposure is required. Transferrin receptor (TfR) is highly expressed at the BBB and can be used to transport such therapeutics across the BBB via a receptor-mediated transcytosis. Mouse models previously have been developed, in which the mouse TfR was replaced with a full-length human TfR cDNA, with the objective of evaluating the ability of potential therapeutics to cross the BBB. However, these transgenic mice were unhealthy and showed abnormally high TfR expression, low red blood cell count, and high serum iron concentration. Yu et al., *Science Trans. Med.,* 6(261):261ra154 (2014). As a result, these existing mouse models are not suited for use as tools to evaluate therapeutics that are capable of crossing the BBB to treat brain diseases; models that are more representative of endogenous TfR expression and phenotype are required.

BRIEF SUMMARY OF THE INVENTION

In one aspect, this disclosure provides a polynucleotide comprising a nucleic acid sequence encoding a chimeric transferrin receptor (TfR) polypeptide that comprises a non-human mammalian transferrin binding site and a heterologous apical domain having an amino acid sequence at least 80% identical to SEQ ID NO:1. In some embodiments, the heterologous apical domain comprises the amino acid sequence of SEQ ID NO:1. In some embodiments, the heterologous apical domain comprises the amino acid sequence of SEQ ID NO:7, SEQ ID NO:8, or SEQ ID NO:9.

In some embodiments, the non-human mammalian transferrin binding site is a native (e.g., from the same species as the transmembrane and/or intracellular domain of the TfR) transferrin binding site, e.g., a native mouse transferrin binding site. In some embodiments, the chimeric TfR polypeptide has at least 80% amino acid sequence identity, or at least 85%, 90%, or 95% identity, to SEQ ID NO:3. In some embodiments, the chimeric TfR polypeptide comprises the amino acid sequence of SEQ ID NO:3. In some embodiments, the region of the nucleic acid sequence encoding the heterologous apical domain of the chimeric TfR polypeptide has at least 70% nucleotide sequence identity to SEQ ID NO:2. In some embodiments, the region of the nucleic acid sequence encoding the heterologous apical domain of the chimeric TfR polypeptide comprises the nucleotide sequence of SEQ ID NO:2. In some embodiments, the polynucleotide encoding the chimeric TfR comprises exons and introns of a mouse transferrin receptor gene and the nucleic acid sequence encoding the heterologous apical domain is positioned after the fourth exon of a mouse transferrin receptor gene to replace the apical binding domain of the mouse transferrin receptor gene.

In another aspect, provided herein is a chimeric TfR polypeptide that comprises a non-human mammalian transferrin binding site and a heterologous apical domain having an amino acid sequence at least 80% identical to SEQ ID NO:1. In some embodiments, the chimeric TfR polypeptide comprises a native TfR polypeptide in which only the native apical domain is replaced by a heterologous apical domain. In some embodiments, a chimeric TfR polypeptide comprises a native TfR binding site and an apical binding domain that is heterologous to the native TfR binding site, e.g., wherein at least one domain, or region thereof, in addition to the apical domain comprises a non-native amino acid sequence. In some embodiments, the heterologous apical domain comprises the amino acid sequence of SEQ ID NO:1. In some embodiments, the heterologous apical domain comprises the amino acid sequence of SEQ ID NO:7, SEQ ID NO:8, or SEQ ID NO:9. In some embodiments, the chimeric TfR has at least 80%, 90%, 95%, or 98% amino acid sequence identity to SEQ ID NO: 3. In some embodiments, the chimeric TfR polypeptide comprises the amino acid sequence of SEQ ID NO:3.

In a further aspect, provided herein are host cells that express a chimeric transferrin receptor as described above. In some embodiments, a host cell comprises a polynucleotide that encodes the chimeric transferrin receptor polypeptide. In some embodiments, the host cell is a mouse cell. In some embodiments, the chimeric TfR polypeptide expressed by the host cell comprises (a) a heterologous apical domain in place of the endogenous apical domain of the TfR polypeptide and (b) the endogenous transferrin binding site. In some embodiments, the heterologous apical domain has an amino acid sequence at least 80% identical to SEQ ID NO: 1. In some embodiments, the host cell expresses a chimeric TfR in which only the apical domain of the endogenous TfR is replaced by a heterologous apical domain. In some embodiments, a host cell expresses a chimeric TfR comprising an endogenous TfR binding site and a heterologous apical domain, e.g., wherein at least one domain, or region thereof, in addition to the apical domain comprises a non-native amino acid sequence. In some embodiments, the heterologous apical domain comprises the amino acid sequence of SEQ ID NO:1. In some embodiments, the nucleic acid sequence that encodes the heterologous apical domain in the cell comprises the nucleotide sequence of SEQ ID NO:2. In some embodiments, the host cell is a mouse cell. In some embodiments, the nucleic acid sequence encoding the apical domain in the cell is positioned after the fourth exon of a mouse transferrin receptor gene. In some embodiments, the host cell is ex vivo. In some embodiments, the host cell is an embryonic stem cell. In some embodiments, the genome of the host cell comprises a deletion of the apical domain of the native TfR.

In an additional aspect, the disclosure provides a non-human transgenic animal that expresses a chimeric TfR polypeptide, wherein the chimeric TfR polypeptide comprises a heterologous apical domain that replaces the apical domain of the TfR polypeptide endogenous to the non-human transgenic animal. In some embodiments, the genome of the non-human transgenic animal comprises a transferrin receptor gene that encodes a heterologous apical domain in place of the apical domain of the endogenous TfR of the non-human transgenic animal. In some embodiments, the non-human transgenic animal expresses a chimeric TfR comprising a heterologous apical domain in place of the native domain of the TfR of the non-human transgenic animal and a native transferrin binding site. In some embodiments, a non-human transgenic animal expresses a chimeric transferrin receptor in which only the apical domain of the endogenous transferrin receptor is replaced by a heterologous apical domain. In some embodiments, a non-human transgenic animal expresses a chimeric TfR polypeptide comprising an endogenous TfR binding site and an apical binding domain that is heterologous to the endogenous TfR binding site, e.g., wherein at least one domain, or region thereof, in addition to the apical domain comprises a non-native amino acid sequence. In some embodiments, the non-human transgenic animal comprises the host cells as described above. In some embodiments, the transgenic animal is a rodent. In some embodiments, the transgenic animal is a mouse or a rat. In some embodiments, the transgenic animal is homozygous for the chimeric TfR. In some embodiments, the transgenic animal is heterozygous for the chimeric TfR.

In another aspect, provided herein is a method of screening for an apical domain binding polypeptide (ADBP) that binds to a chimeric TfR, the method comprising contacting a candidate ADBP with a chimeric TfR polypeptide as described above; and determining the amount of the candidate ADBP that binds to the chimeric TfR polypeptide. In some embodiments, the step of contacting the candidate ADBP with the chimeric TfR polypeptide comprises contacting the ADBP with a host cell that expresses the chimeric TfR polypeptide. In some embodiments, the step of contacting the candidate ADBP with the chimeric TfR polypeptide comprises contacting the ADBP with an endothelium that expresses the chimeric TfR polypeptide. In some embodiments, the endothelium is a blood-brain barrier endothelium. In some embodiments, the amount of the candidate ADBP that binds the chimeric TfR polypeptide is determined by immunoassay. In some embodiments, the amount of the candidate ADBP that binds the chimeric TfR polypeptide is determined by surface plasmon resonance. In some embodiments, wherein contacting step is performed is in vivo. In some embodiments the candidate ADBP is coupled to an effector molecule. In some embodiments, the effector molecule is a small molecule, RNA, DNA, or polypeptide. In some embodiments, the effector molecule is a polypeptide. In some embodiments, the polypeptide is an antibody or an antigen-binding fragment thereof.

In yet another aspect, provided herein is a method of measuring the amount of an ADBP that binds to a chimeric TfR polypeptide, the method comprising contacting the ADBP with a chimeric TfR polypeptide disclosed above; and determining the amount of ADBP bound to the chimeric TfR polypeptide by immunoassay or surface plasmon resonance.

In yet another aspect, provided herein is a method of screening for an ADBP that crosses the blood-brain barrier, the method comprising: (a) administering an ADBP that binds an apical domain having at least 80% amino acid sequence identity to SEQ ID NO:1 to a non-human transgenic animal as disclosed herein; and (b) measuring the presence or an activity of the ADBP in the brain of the non-human transgenic animal. In some embodiments, the ADBP is coupled to an effector molecule. In some embodiments, the effector molecule is a small molecule, RNA, DNA, or polypeptide. In some embodiments, the polypeptide is an antibody or an antigen-binding fragment thereof.

In some embodiments, the determining step comprises performing a quantitative immunoassay. In some embodiments, the measuring step comprises contacting the brain or brain tissue of the animal with an agent that binds to the effector molecule to determining the level of the effector molecule in the brain. In some embodiments, the measuring step comprises measuring a pharmacodynamic (PD) effect of the effector molecule. In some embodiments, the effector molecule is an anti-BACE1 antibody or an antigen-binding fragment thereof and the measuring step comprises measuring the level of soluble ABeta40 in the brain. In some embodiments, the effector molecule is an antibody or an antigen-binding fragment thereof that binds to a target in the brain.

In another aspect, provided herein is a method of monitoring an ADBP that crosses the blood-brain barrier, the method comprising: (a) administering an ADBP that binds an apical domain having at least 80% amino acid sequence identity to SEQ ID NO:1 to a non-human transgenic animal as disclosed herein; and (b) measuring the presence or an activity of the ADBP in the brain of the non-human transgenic animal. In some embodiments, the ADBP is coupled to an effector molecule. In some embodiments, the effector molecule is a small molecule, RNA, DNA, or polypeptide. In some embodiments, the polypeptide is an antibody or an antigen-binding fragment thereof. In some embodiments, the determining step comprises performing a quantitative immunoassay. In some embodiments, the determining step comprises contacting the effector molecule with an agent that binds to the effector molecule and determining the level of level of the effector molecule present in the brain. In some embodiments, the effector molecule is an antibody or an antigen-binding fragment thereof that binds to a target in the brain. In some embodiments, the measuring step comprises measuring a PD effect of the effector molecule binding to the target. In some embodiments, the effector molecule is an anti-BACE1 antibody or an antigen-binding fragment thereof and the measuring step comprises measuring the level of soluble ABeta40 in the brain.

In yet another aspect, provided herein is a method of generating a transgenic non-human single cell embryo that expresses a chimeric transferrin receptor (TfR) polypeptide, the method comprising replacing the apical domain of the endogenous TfR in the non-human single cell embryo with a heterologous apical domain having at least 80% identity to SEQ ID NO:1. In some embodiments, replacing the apical domain is performed by homologous recombination. In some embodiments, the method comprises contacting a Cas9 protein, at least one single guide RNA (sgRNA), and a donor DNA comprising a nucleic acid sequence encoding the heterologous apical domain, wherein the heterologous apical domain is flanked by a left homology arm and a right homology arm, such that the heterologous apical domain coding sequence replaces the apical domain of the endogenous TfR in the genome of the non-human single cell embryo. In some embodiments, the heterologous apical domain is codon-optimized for expression in the non-human single cell embryo. In some embodiments the non-human single cell embryo is a mouse embryo. In some embodiments, the donor DNA is positioned after the fourth exon of a mouse transferrin receptor gene.

In yet another aspect, provided herein is a method of generating a non-human transgenic animal comprising (a) transferring the transgenic non-human single cell embryo disclosed above to a pseudo pregnant female of the same animal species as the non-human single cell embryo, and (b) selecting a non-human transgenic animal from the progeny produced by the female, wherein the non-human transgenic animal comprises a chimeric transferrin receptor (TfR) polypeptide in which the apical domain of an endogenous TfR has been replaced with a heterologous apical domain having an amino acid sequence of at least 80% identity to SEQ ID NO:1.

In yet another aspect, provided herein is a method of generating a non-human transgenic animal that expresses a chimeric transferrin receptor (TfR) polypeptide, the method comprising (a) introducing into an embryonic cell of the animal a polynucleotide encoding an apical domain having at least 80% identity to SEQ ID NO:1, wherein the polynucleotide is targeted to a region of an endogenous TfR gene that encodes an endogenous TfR apical domain and wherein the polynucleotide encoding the apical domain having at least 80% identity to SEQ ID NO:1 replaces the region of the endogenous TfR gene that encodes the endogenous apical domain, and (b) developing the cell or progeny thereof into a non-human transgenic animal.

The foregoing general description and the following detailed description are exemplary and explanatory and are intended to provide further explanation of the invention as claimed. Other objects, advantages and novel features will be readily apparent to those skilled in the art from the following detailed description of the invention.

BRIEF DESCRIPTION OF THE DRAWINGS

FIG. 4A shows plasma huIgG1 concentration in hUTfR$^{apical+/+}$ mice 24 hours after the mice were administered with 50 mg/kg of anti-TfR/BACE1 or anti-BACE1. The results showed that TfR-mediated clearance of anti-TfR/BACE1 was enhanced relative to that of anti-BACE1. FIG. 4B shows mean brain uptake of anti-TfR/BACE1 following a systemic dosing of the antibody. The results show an increase of about 28-fold of the accumulation of anti-TfR/BACE1 as compared to that of anti-BACE1 in mouse brains. FIG. 4C shows that A-beta in the brain was reduced by 49% in mice treated with anti-TfR/BACE1 as compared to mice treated with anti-BACE1. FIG. 4D shows a reduction in the plasma A-beta level in huTfR$^{apical+/+}$ mice that had been treated with anti-BACE1 or anti-TfR/BACE1 as compared to untreated wild-type mice. All graphs represent mean±SD, n=8 per group (n=2 for untreated wild-type mice).

DETAILED DESCRIPTION OF THE INVENTION

Figure 1C:
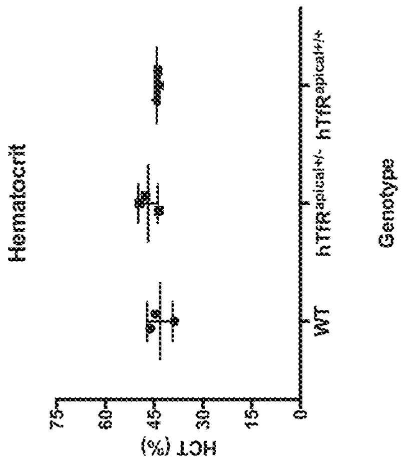
FIGS. 1A-1C show the results of a complete blood count analysis of wild-type, huTfR$^{apical+/-}$, and huTfR$^{apical+/+}$ mice. No genotype-specific differences were observed in total red blood cells, hemoglobin, or hematocrit. Graphs in the figure represent mean±SD, n=3 per group.

We have developed chimeric forms of the transferrin receptor that include a non-human (e.g., mouse) mammalian transferrin binding site and an apical domain that is heterologous to the domain containing the transferrin binding site. These chimeric receptors can be expressed in transgenic animals, particularly where the transferrin binding site is derived from the transgenic animal species and where the apical domain is derived from a primate (e.g., human or monkey). The present invention therefore provides a polynucleotide encoding a chimeric transferrin receptor that comprises a non-human mammalian transferrin binding site and an apical domain having an amino acid sequence at least 80% identical to SEQ ID NO:1. The invention also provides a non-human, for example, non-primate, transgenic animal expressing such chimeric TfRs and the use of the non-human transgenic animal to screen for polypeptides that can cross the BBB by binding to human transferrin receptor (huTfR) in vivo. In some embodiments, the non-human transgenic animal contains a native transferrin receptor (such as a mouse transferrin receptor (mTfR)), in which the apical domain is replaced with an orthologous apical domain having an amino acid sequence at least 80% identical to SEQ ID NO:1, thereby leaving the native transferrin binding site and the majority, e.g., at least 70%, or at least 75%, of the sequence encoding the transferrin receptor intact. This non-human transgenic animal thus maximally retains the transferrin-binding functionality of the endogenous transferrin receptor of the non-human animal, including the ability to maintain proper iron homeostasis as well as bind and transport transferrin. As a result, the transgenic animal is healthy and suitable for use in discovery and development of therapeutics for treating brain diseases.

Terminology

As used herein, the singular forms "a," "an," and "the" include plural referents unless the content clearly dictates otherwise. Thus, for example, reference to "an antibody" optionally includes a combination of two or more such molecules, and the like.

As used herein, the terms "about" and "approximately," when used to modify an amount specified in a numeric value or range, indicate that the numeric value as well as reasonable deviations from the value known to the skilled person in the art, for example, ±20%, ±10%, or ±5%, are within the intended meaning of the recited value.

A "transferrin receptor" as used herein refers to transferrin receptor protein 1. The human transferrin receptor 1 polypeptide sequence is set forth in SEQ ID NO:6. Transferrin receptor protein 1 sequences from other species are also known (e.g., chimpanzee, accession number XP_003310238.1; rhesus monkey, NP_001244232.1; dog, NP_001003111.1; cattle, NP_001193506.1; mouse, NP_035768.1; rat, NP_073203.1; and chicken, NP_990587.1). The term "transferrin receptor" also encompasses allelic variants of exemplary reference sequences, e.g., human sequences, that are encoded by a gene at a transferrin receptor protein 1 chromosomal locus. Full length transferrin receptor protein includes a short N-terminal intracellular region, a transmembrane region, and a large extracellular domain. The extracellular domain is characterized by three domains: a protease-like domain, a helical domain, and an apical domain.

The term "chimeric TfR" as used herein refers to a transferrin receptor protein that has all or a subregion of the apical domain replaced with a corresponding apical domain region from a heterologous transferrin receptor.

A "transferrin binding site" as used herein refers to regions in the helical and protease-like domain of a TfR protein that mediate binding of transferrin, e.g., iron-bound transferrin, to the receptor. The transferrin binding site is distal to the apical domain.

A "non-human mammalian transferrin binding site" as used herein refers to a sequence from the transferrin binding site of the native transferrin receptor of a non-human mammal, or a functional derivative thereof that is capable of binding to the native non-human mammalian transferrin. In some embodiments, the non-human mammalian transferrin binding site comprises an amino acid sequence that is at least 80%, at least 90%, at least 95%, or at least 98% identical to the transferrin binding site of the native transferrin receptor of the non-human mammal. Examples of the non-human mammals include mouse, rat, rabbit, bovine, ovine, canine, feline, equine, porcine, non-human primates, and the like.

As used herein, an "huTfR$^{apical+/+}$ mouse" refers to a transgenic mouse in which the apical domain of the mouse transferrin receptor has been replaced with the apical domain of a human transferrin receptor, and the transgenic mouse being homozygous for the transgene.

As used herein, an "huTfR$^{apical+/-}$ mouse" refers to a transgenic mouse in which the apical domain of the mouse transferrin receptor has been replaced with the apical domain of a human transferrin receptor; and the transgenic mouse being heterozygous for the transgene.

As used herein, the terms "wild-type," "native," and "naturally occurring" with respect to a transferrin receptor or a domain thereof, refer to a transferrin receptor or a domain thereof that has a sequence that occurs in nature.

An "endogenous" transferrin receptor or domain thereof as used herein refers to a transferrin receptor that naturally occurs in a cell or non-human animal, i.e., in the absence of genetic modification to the cell or animal.

As used herein, the term "heterologous" with respect to a domain of a transferrin receptor, e.g., the apical domain, refers to a domain of the transferrin receptor that is expressed outside its native context, e.g., separated from transferrin receptor sequences with which it typically is in proximity in nature, or adjacent (or contiguous with) transferrin receptor sequences with which it typically is not in proximity.

The term "amino acid" refers to naturally occurring and synthetic amino acids, as well as amino acid analogs and amino acid mimetics that function in a manner similar to the naturally occurring amino acids.

Naturally-occurring amino acids are those encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Amino acids may be referred to herein by either their commonly known three letter symbols or by the one-letter symbols recommended by the IUPAC-IUB Biochemical Nomenclature Commission.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. Amino acid polymers may comprise entirely L-amino acids, entirely D-amino acids, or a mixture of L and D amino acids.

"Conservatively modified variant" refers to an alteration that results in the substitution of an amino acid with another amino acid that can be categorized as having a similar feature. Examples of categories of conservative amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R), and His (Histidine or H); an "aromatic group" including Phe (Phenylalanine or F), Tyr (Tyrosine or Y), Trp (Tryptophan or W), and (Histidine or H); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T), and Cys (Cysteine or C). Within each group, subgroups can also be identified. For example, the group of charged or polar amino acids can be sub-divided into sub-groups including: a "positively-charged sub-group" comprising Lys, Arg and His; a "negatively-charged sub-group" comprising Glu and Asp; and a "polar sub-group" comprising Asn and Gln. In another example, the aromatic or cyclic group can be sub-divided into sub-groups including: a "nitrogen ring sub-group" comprising Pro, His and Trp; and a "phenyl sub-group" comprising Phe and Tyr. In another further example, the aliphatic group can be sub-divided into sub-groups, e.g., an "aliphatic non-polar sub-group" comprising Val, Leu, Gly, and Ala; and an "aliphatic slightly-polar sub-group" comprising Met, Ser, Thr, and Cys. Examples of categories of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —$NH_2$ can be maintained. In some embodiments, hydrophobic amino acids are substituted for naturally occurring hydrophobic amino acid, e.g., in the active site, to preserve hydrophobicity.

The terms "identical" or percent "identity," in the context of two or more polypeptide sequences, refer to two or more sequences or subsequences that are the same or have a specified percentage of amino acid residues, e.g., at least 60% identity, at least 65%, at least 70%, at least 75%, at least 80%, at least 85%, at least 90%, or at least 95% or greater, that are identical over a specified region when compared and aligned for maximum correspondence over a comparison window, or designated region as measured using one a sequence comparison algorithm or by manual alignment and visual inspection.

For sequence comparison of polypeptides, typically one amino acid sequence acts as a reference sequence, to which a candidate sequence is compared. Alignment can be performed using various methods available to one of skill in the art, e.g., visual alignment or using publicly available software using known algorithms to achieve maximal alignment. Such programs include the BLAST programs, ALIGN, ALIGN-2 (Genentech, South San Francisco, Calif.) or Megalign (DNASTAR). The parameters employed for an alignment to achieve maximal alignment can be determined by one of skill in the art. For sequence comparison of polypeptide sequences for purposes of this application, the BLASTP algorithm standard protein BLAST for aligning two proteins sequence with the default parameters is used.

The term "comprising" is intended to mean that the compositions and methods include the recited elements, but do not exclude others. "Consisting essentially of" when used to define compositions and methods, refers to the specified materials or steps and those that do not materially affect the basic and novel characteristic(s) of the claimed invention. "Consisting of" shall mean excluding more than trace amounts of other ingredients and substantial method steps recited. Embodiments defined by each of these transition terms are within the scope of this invention.

The terms "polynucleotide," "nucleic acid," and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double and single stranded molecules. Unless otherwise specified or required, any embodiment of this invention that is a polynucleotide encompasses both the double stranded form and each of two complementary single stranded forms known or predicted to make up the double stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule.

The term "knock-in" refers to a one-for-one substitution of DNA sequence information in a predetermined genetic locus or the insertion of sequence information not found within the locus. Those skilled in the art will readily appreciate how to use various genetic approaches, e.g., CRISPR/Cas9 systems, ZFN, TALEN, transposon-mediated insertion, to knock in a target polynucleotide sequence in a specific locus of the genome.

The term "blood-brain barrier" or "BBB" refers to a highly selective semipermeable membrane barrier that separates the circulating blood from the brain extracellular fluid in the central nervous system (CNS). The blood-brain barrier is formed by brain endothelial cells, which are connected by tight junctions.

Transferrin Receptor

A transferrin receptor mediates cellular uptake of iron via receptor-mediated endocytosis of ligand-occupied transferrin receptor. TfR is present both in human and non-human species, such as non-human primates and rodents. The native human TfR (huTfR), Uniprot P02786, SEQ ID NO:6, is a homodimeric type II transmembrane protein; it has a cytoplasmic domain, a transmembrane region, and an extracellular domain, which comprises an apical domain and a transferrin-binding domain. Each monomer of the huTfR has three structurally distinct domains: a protease-like domain proximal to the membrane, a helical domain accounting for all the dimer contacts, and a membrane-distal apical domain (Lawrence et al., *Science,* 286 (1999), pp. 779-782). HuTfR dimer has a molecular weight of about 190,000 Daltons. The apical domain of the huTfR, which has a sequence of SEQ ID NO:1 (encoded by SEQ ID NO:2), does not participate in the interaction between transferrin and TfR. It has been speculated that this domain may provide contact surface for other proteins to bind the TfR. The native cynomolgous monkey, native rhesus monkey, and native chimpanzee TfRs are also known, as represented, for example, by accession numbers XP_005545315, NP_001244232.1, and XP_003310238.1, respectively. The apical domain of the native cynomolgous monkey, native rhesus monkey, and native chimpanzee TfRs share about 96%, 95%, and 98% sequence identity, respectively, with the apical domain of the native human TfR of SEQ ID NO:1.

The native mouse TfR (mTfR), Uniprot Q62351, SEQ ID NO:5 has about 77% amino acid sequence identity with huTfR. The apical domain of the native mTfR is about 74% identical to that of the native huTfR. The mTfR contains the three structurally distinct domains that are similar to the human counterparts. The complete gene sequence for mouse TfR, with annotated exons and introns, can be found from the NCBI database (Gene ID: 22042). Mouse TfR is found on chromosome 16 (NCBI reference sequence NC_000082.6).

One aspect includes a chimeric TfR polypeptide. In some embodiments, the chimeric TfR comprises a non-human mammalian transferrin binding site and a heterologous apical domain that shares an amino acid sequence identity, e.g., at least 75%, at least 77%, at least 80%, at least 85%, at least 90%, or at least 95%, with the apical domain of huTfR, SEQ ID NO:1. In some embodiments, the heterologous apical domain has a sequence of SEQ ID NO:1, SEQ ID NO:7, SEQ ID NO:8, or SEQ ID NO:9.

The non-human mammalian transferrin binding site of the chimeric TfR allows for the specific binding of the non-mammalian transferrin to the chimeric TfR. In some embodiments, the non-human mammalian transferrin binding site is a native transferrin binding site, e.g., a mouse transferrin receptor binding site.

In some embodiments, a chimeric TfR polypeptide comprises a native TfR polypeptide in which only the native apical domain is replaced by a heterologous apical domain.

In some embodiments, a chimeric TfR polypeptide comprises a native TfR binding site and an apical binding domain that is heterologous to the native TfR binding site, e.g., wherein at least one domain, or region thereof, in addition to the apical domain has a non-native amino acid sequence.

In some embodiments, the chimeric TfR polypeptide has at least 80%, at least 85%, at least 85%, at least 92%, at least 95%, or at least 98% amino acid sequence identity to SEQ ID NO:3. In one embodiment, the polynucleotide encoding the chimeric TfR polypeptide comprises exons and introns of a mouse transferrin receptor gene and a nucleic acid sequence encoding the huTfR apical domain. In one embodiment, a non-human mammalian TfR apical domain is replaced by a huTfR apical domain coding sequence, for example by replacing the corresponding exons in the non-human mammalian TfR gene with a huTfR apical domain sequence. In an exemplary embodiment, the non-human mammalian TfR gene is a mouse TfR gene. In one embodiment, a mTfR apical domain is replaced by a huTfR apical domain coding sequence, which is positioned, for example, after the fourth exon of the mouse transferrin receptor gene in order to produce the chimeric TfR.

In some aspects, the invention provides isolated nucleic acids comprising a nucleic acid sequence encoding any of the polypeptides comprising a chimeric TfR polypeptide described herein. In some embodiments, the region of the nucleic acid sequence encoding the heterologous apical domain in the chimeric TfR polypeptide shares a nucleic acid sequence identity of at least 75%, at least 77%, at least 80%, at least 85%, at least 90%, or at least 95% with the coding sequence of the apical domain of the native huTfR, SEQ ID NO:2.

In another aspect, polynucleotides are provided that comprise a nucleotide sequence that encodes the chimeric transferrin receptor described herein. The polynucleotides may be single-stranded or double-stranded. In some embodiments, the polynucleotide is DNA. In particular embodiments, the polynucleotide is cDNA. In some embodiments, the polynucleotide is RNA.

Codon Optimization

In some embodiments, the coding sequence for the chimeric TfR, especially the sequence that encodes the huTfR apical domain, is codon optimized in order to improve the expression of the chimeric TfR in mouse. Methods for codon optimization are readily available, for example, optimizer, which is accessible at genomes.urv.es/OPTIMIZER, and GeneGPS® Expression Optimization Technology from DNA 2.0 (Newark, Calif.). In a preferred embodiment, the coding sequence is codon-optimized for expression in mouse using the OptimumGene' algorithm from GenScript (Piscataway, N.J.).

Methods for Replacing the Apical Domain of the Non-Human Mammalian Transferrin Receptor with a Desired Apical Domain A non-human transgenic animal comprising a knock-in of a heterologous apical domain as disclosed herein can be generated using a variety of methods, for example, a zinc finger nuclease (ZFN), a Tale-effector domain nuclease (TALEN), a transposon-mediated system, and the CRIPSR/Cas9 system. These methods typically comprise administering to the cell one or more polynucleotides encoding one or more nucleases such that the nuclease mediates modification of the endogenous gene by cleaving the DNA to create 5' and 3' cut ends in the DNA strand. In the presence of a donor sequence that is flanked by a left and a right homology arms that are substantially homologous to a sequence extending 5' from the 5' end and a sequence extending 3' from the 3' end, the donor is integrated into the endogenous gene targeted by the nuclease via homology-directed repair (HDR). In some embodiments, the knock-in is conducted using the CRISPR/Cas9 system. For example, a nucleic acid sequence encoding a heterologous apical domain is introduced into an endogenous TfR gene to generate a chimeric TfR, which results in that the naturally occurring sequences that encodes the apical domain is replaced but the overall structure of the gene is maintained.

CRISPR

In some embodiments, the knock-in of the apical domain that is at least 80% identical to SEQ ID NO:1 is performed using the CRIPSR/Cas9 system. The CRISPR/Cas9 system includes a Cas9 protein and at least one to two ribonucleic acids that are capable of directing the Cas9 protein to and hybridizing to a target motif in the apical domain of the transferrin receptor that is to be replaced. These ribonucleic acids are commonly referred to as the “single guide RNA” or “sgRNA.” The Cas9 protein then cleaves the target motif, which results in a double-strand break or a single-strand break. In the presence of a donor DNA that comprises huTfR apical domain coding sequence flanked by two homology arms, the donor DNA is inserted into the target transferrin receptor DNA, replacing the apical domain.

The Cas9 protein used in the invention can be a naturally occurring Cas9 protein or a functional derivative thereof. A “functional derivative” of a native sequence polypeptide is a compound having a qualitative biological property in common with a native sequence polypeptide. “Functional derivatives” include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative of Cas9 to hydrolyze a DNA substrate into fragments. Suitable functional derivatives of a Cas9 polypeptide or a fragment thereof include but are not limited to mutants, fusions, covalent modifications of Cas9 protein or a fragment thereof.

In some embodiments, the Cas9 protein is from *Streptococcus pyogenes*. Cas9 contains 2 endonuclease domains, including a RuvC-like domain which cleaves target DNA that is noncomplementary to the sgRNA, and an HNH nuclease domain which cleave target DNA complementary to sgRNA. The double-stranded endonuclease activity of Cas9 also requires that a short conserved sequence (2-5 nucleotides), known as a protospacer-associated motif (PAM), follows immediately 3' of a target motif in the target sequence. In some embodiments, the PAM motif is an NGG motif. In one illustrative embodiment, the apical domain in a mouse is replaced by using the Cas9 protein, which is directed by sgRNAs to the region between exons 4 and 9 of the mouse gene. A donor DNA is introduced to the reaction. The donor DNA comprises a human apical domain coding sequence that is between a left homology arm that is homologous to the mouse TfR sequence starting upstream of exon 4 and a right homology arm that is homologous to the mouse TfR sequence starting within exon 9. In certain embodiments, the left homology arm overlaps the mouse TfR sequence by 817 nucleotides, starting upstream of exon 4, and the right homology arm overlaps the mouse TfR sequence by 807 nucleotides, starting within exon 9. As a result, the nucleotide sequence encoding a desired apical domain, such as the one that has an amino acid sequence at least 80% identical to SEQ ID NO:1, can be inserted after the fourth mouse exon, and the inserted nucleotide sequence is flanked at the 3' end by the appropriately following mouse exon. In some embodiments, the human apical domain coding sequence that is inserted into the mouse TfR gene is codon-optimized for mouse expression.

The sgRNAs can be selected depending on the particular CRISPR/Cas9 system employed and the sequence of the target polynucleotide. In some embodiments, the one to two ribonucleic acids are designed to hybridize to a target motif immediately adjacent to a deoxyribonucleic acid motif recognized by the Cas9 protein. In some embodiments, each of the one to two ribonucleic acids are designed to hybridize to target motifs immediately adjacent to deoxyribonucleic acid motifs recognized by the Cas9 protein, wherein the target motifs flank the genomic sequence to be replaced. Guide RNAs can be designed using software that is readily available, for example, at crispr.mit.edu. Illustrative sgRNAs that can be used to generate a chimeric TfR transgenic mouse include SEQ ID NOs:10-11.

The donor DNA as disclosed herein comprises a nucleotide sequence that encodes an amino acid sequence at least 75% identical to SEQ ID NO:1. In some embodiments, the donor DNA comprises a sequence encoding SEQ ID NO:1 or encoding a sequence that shares at least 75%, at least 77%, at least 80%, at least 85%, at least 90%, or at least 95% amino acid sequence identity with SEQ ID NO:1. In some embodiments, the donor DNA comprises the nucleotide sequence of SEQ ID NO:2 or a sequence that shares at least 60%, at least 70%, at least 77%, at least 80%, at least 85%, at least 90%, or at least 95% sequence identity with SEQ ID NO:2. The donor DNA as disclosed herein further comprises a left homology arm and a right homology arm that flank the apical domain coding sequence and are designed to overlap the 5' and 3' exon sequences relative to the cleave site by the Cas9 protein. The homology arms may extend beyond the 5' and 3' exon sequences, and each of the homology arms may be at least 20, 30, 40, 50, 100, or 150 nucleotides in length. One of skilled in the art can readily determine the optimal length of the homology arm required for the experiment. In one illustrative embodiment, the left homology arm of the donor DNA spans nucleotides 1-817 of SEQ ID NO:4 and the right homology arm spans nucleotides 1523-2329 of SEQ ID NO:4. In some embodiments, the left homology arm shares at least 85%, at least 90%, at least 95%, or at least 98% sequence identity to nucleotides 1-817 of SEQ ID NO:4. In some embodiments, the right homology arm shares at least 85%, at least 90%, at least 95%, or at least 98% sequence identity to nucleotides 1523-2329 of SEQ ID NO:4.

In some embodiments, the sgRNAs can also be selected to minimize hybridization with nucleic acid sequences other than the target polynucleotide sequence. In some embodiments, the one to two ribonucleic acids are designed to hybridize to a target motif that contains at least two mismatches when compared with all other genomic nucleotide sequences in the cell to minimize off-target effects of the CRISPR/Cas9 system. Those skilled in the art will appreciate that a variety of techniques can be used to select suitable target motifs for minimizing off-target effects (e.g., bioinformatics analyses). Methods of using the CRISPR/Cas9 system to reduce gene expression are described in various publications, e.g., US Pat. Pub. Nos. 2014/0170753 and 2016/0257974, the disclosures of which hereby are incorporated by reference in their entirety.

Zinc Finger Nuclease (ZFN)

In some embodiments, the chimeric TfR is produced by knocking-in the huTfR apical domain using a ZFN. ZFNs are fusion proteins that comprise a non-specific cleavage domain (N) of FokI endonuclease and a zinc finger protein (ZFP). A pair of ZNFs are involved to recognize a specific locus in a target gene: one that recognizes the sequence upstream and the other that recognizes the sequence downstream of the site to be modified. The nuclease portion of the ZFN cuts at the specific locus. The donor DNA as described above can then be inserted into the specific locus. Methods of using the ZFNs to reduce gene expression are well known, for example, as disclosed in U.S. Pat. No. 9,045,763 and also in Durai et al., "Zinc Finger Nucleases: Custom-Designed Molecular Scissors for Genome Engineering of Plant and Mammalian cells," *Nucleic Acid Research,* 33 (18):5978-5990 (2005), the disclosures of which are incorporated by reference in their entirety.

Transcription Activator-Like Effector Nucleases (TALENs)

In some embodiments, the chimeric TfR is produced by knocking-in the huTfR apical domain with TALENs. TALENs are similar to ZFNs in that they bind as a pair around a genomic site and direct the same non-specific nuclease, Fokl, to cleave the genome at a specific site, but instead of recognizing DNA triplets, each domain recognizes a single nucleotide. Methods of using the ZFNs to reduce gene expression are also well known, for example, as disclosed in U.S. Pat. No. 9,005,973 and also Christian et al., "Targeting DNA Double-Strand Breaks with TAL Effector Nucleases," *Genetics,* 186(2): 757-761 (2010), the disclosures of which are incorporated by reference in their entirety.

Host Cells/Transgenic Animals Expressing the Chimeric TfR

In some embodiments, the invention provides a host cell that expresses the chimeric TfR, e.g., comprising a nucleic acid sequence encoding the chimeric transferrin receptor described above. In some embodiments, the host cell is a non-human mammalian cell. Any of knock-in methods described above, i.e., CRISPR, TALEN, Zinc finger nuclease, can be used to replace the apical domain of the native transferrin receptor in the host cells with a heterologous apical domain that has an amino acid sequence at least 80% identical to SEQ ID NO:1. In some embodiments, the host cell is eukaryotic, e.g., a mouse cell at least 80% identical to SEQ ID NO:1. In some cases, the host cell is contacted with the sgRNA and Cas9, a donor DNA that comprises the nucleic acid sequence encoding the heterologous apical domain, the nucleic acid sequence being flanked with a left and a right homology arms. The sgRNA and homology arms having sequences such that the heterologous apical domain coding sequence is inserted into the location in the genome to replace the coding sequence of the apical domain of the native transferrin receptor in the host cell. In some embodiments, the host cell is a cell from a non-primate mammal, such as a mouse, rat, rabbit, bovine, ovine, canine, feline, equine, porcine, and the like.

In some embodiments, the method of knock-in is performed in an embryonic stem (ES) cell to produce an ES cell that expresses the chimeric transferrin receptor polypeptide. The embryonic stem cell may then be developed into a progeny cell or a non-human transgenic animal whose genome comprises the nucleic acid encoding the chimeric transferrin receptor polypeptide. In some embodiments, the ES cell is introduced into blastocysts and transferred into pseudo pregnant females. In some cases, a founder male harboring the transgene can be selected and bred to wild-type females to generate F1 heterozygous mice. Homozygous non-human animals can be subsequently generated from breeding of F1 generation heterozygous non-human animals. Methods for culturing ES cells and introducing nucleotide sequences to target the genome of an ES cell to produce a transgenic animal are well known, for example, as described in Ramirez-Solis et al., "Gene targeting in mouse embryonic stem cells," *Methods Enzymol.,* 225:855-878 (1993); and US Pat. Pub. No. 2013/0318643, the disclosures of which are incorporated by reference in their entirety. In some embodiments, embryonic stem cells from a transgenic animal that has a chimeric TfR of the present invention can be used as a source to provide progeny of the transgenic animal.

In some embodiments, the method of knocking-in is carried out in single-cell non-human animal. In one illustrative embodiment, sgRNAs, Cas9, and a donor polynucleotide comprising the apical domain coding sequence that is at least 80% identical to SEQ ID NO:1, where the coding sequence being flanked by a left homology arm and a right homology arm, are introduced into single cell embryos via pronuclear microinjection. The recipient embryos are then transferred to pseudo pregnant females. The sgRNAs form a complex with the Cas9 protein, which then targets the coding sequence of the apical domain of the transferrin receptor in the non-human animal embryos. As a result, the non-human animal transferrin receptor apical domain is cleaved and replaced with the transferrin receptor apical domain coding sequence from the donor polynucleotide. In some cases, a founder male harboring the transgene can be selected and bred to wild-type females to generate F1 heterozygous mice. Homozygous non-human animals can be subsequently generated from breeding of F1 generation heterozygous non-human animals. The transgenic animals disclosed herein can be a rodent, for example, a mouse or a rat.

In one illustrative embodiment, in part due to the fact that the non-human transgenic animal, e.g., a non-primate mammal, retains introns and the transferrin binding domain of the native TfR, the transgenic animals generated by knocking-in the apical domain that has an amino acid sequence at least 80% identical to SEQ ID NO:1 are generally healthy and demonstrate physiological conditions that are similar to those of wild-type mice of the same species. In one embodiment, all introns outside the apical domain of the TfR are retained. For example, the TfR expression levels are similar to a wild-type animal of the same species; the expression level in the transgenic mouse is no more than 10%, 20%, 30%, 40%, 50%, 60%, 70%, 80%, or 90% less than that of the wild-type mouse or is no more than 10%, 20%, 30%, 40%, 50%, 75%, 100%, 150%, 200%, 300%, or 500% greater than that of the wild-type mouse. The red blood cell count, the level of hemoglobin, and/or hematocrit level are also similar to those in wild-type animals of the same species; the difference is no greater than 50%, e.g., no greater than 40%, no greater than 30%, no greater than 20%, or no greater than 10%. In typical embodiments, transgenic animals in accordance with the invention retain selective BBB transport that enables import of nutrients and proteins and retain the ability to protect CNS from toxins; the presence of transgene doesn't interfere with transferrin binding or FcRn binding to antibodies that bind to the apical domain, described below. Typically, TfR-mediated cellular trafficking in the transgenic animal is also similar to those wild-type animals. The transgenic animals in accordance with the invention are more relevant as a model for pharmacokinetic or pharmacodynamic studies of human BBB-penetrating drugs than the wild-type mice that lack the human TfR entirely or than transgenic animal models that express the entire huTfR extracellular domain (e.g., express the entire huTfR protein).

Although the present invention is illustrated in mouse as shown in the examples, one of ordinary skill in the art would understand that other non-human mammals, for example, rodent, rabbit, bovine, ovine, canine, feline, equine, porcine, camelid, non-human primate, and other mammals, can also be engineered to express the chimeric TfR in a similar fashion, and these transgenic animals can also be used for applications as disclosed herein.

The Apical Domain Binding Polypeptide

An "apical domain binding polypeptide" or "ADBP" as used herein refers to a polypeptide that binds to the apical domain having an amino acid sequence at least 80% identical to SEQ ID NO:1. The ADBP can be an antibody or any polypeptide that is capable of binding to the apical domain of the huTfR of the chimeric TfR. In some embodiments, the ADBP is an agent that is to be delivered across the blood-brain barrier. In some embodiments, the ADBP further comprises an effector molecule coupled to it, e.g., by covalent linkage. The effector molecule may be a therapeutic agent, a labelling agent, or diagnostic agent. In certain embodiments, the effector molecule is a polypeptide, such as a therapeutic or diagnostic antibody, or a polypeptide that has an enzymatic activity or inhibitory activity on an enzyme or a signaling molecule. In certain embodiments, the effector molecule comprises a small molecule, RNA, DNA, or protein.

In some embodiments, the ADBP is a bispecific antibody, with the apical domain binding region being an antibody that recognizes the apical domain and the effector molecule being an antibody that recognizes a different antigen, e.g., an enzyme or a signaling molecule, and the binding of the effector moiety either activates or inhibits the enzyme or the signaling molecule.

Screen for ADBPs that Bind the Chimeric TfR

The chimeric TfRs disclosed herein can be used to screen for ADBPs that are capable of binding to the TfR. The screening method comprises contacting a candidate ADBP with a chimeric TfR disclosed above and determining the amount of candidate ADBP that binds to the chimeric TfR. In some embodiments, the step of contacting the candidate ADBP with the chimeric TfR comprises contacting the ADBP with a host cell that expresses the chimeric TfR. In some cases, the step of contacting the candidate ADBP with the chimeric TfR comprises contacting the ADBP with an endothelium that expresses the chimeric TfR. In some embodiments, the endothelium is a BBB endothelium.

Interactions between the candidate ADBP and TfR can be measured using methods well known in the art, for example, immunoassays or SPR. In some embodiments, the binding of the candidate ADBP to the chimeric TfR is measured by ELISA, a Biacore™ system, or coimmunoprecipitation.

Screen for ADBPs that can Cross the BBB

The non-human transgenic animals expressing the chimeric TfR as described above can be used to characterize the ability of ADBP to bind the apical domain of the chimeric TfR and ultimately the ability to cross the BBB.

Typically, to evaluate the ability of an ADBP to cross BBB, the ADBP is administered to the transgenic animal carrying the chimeric TfR disclosed herein, preferably through intravenous injection. After a period of time, e.g., at least 10 min, at least 20 min, at least 30 min, at least 60 min, at least 90 min, at least 120 min, at least 180 min, or at least 240 min, the transgenic animal is sacrificed and brain tissues are analyzed to determine the presence of the ADBP. The presence of the ADBP can be determined by assaying for the presence of the ADBP and/or an effector molecule joined thereto. In some embodiments, the brain tissues are perfused with saline, e.g., PBS, and fixed before detection. The presence of the effector molecule in the sections can be detected using standard imaging methods, for example, immunohistochemical or immunofluorescent methods. A positive detection of the effector molecule in the brain tissue indicates that the effector molecule can cross the BBB. In some cases, determining the presence of the ADBP in the brain comprises performing a quantitative immunoassay. The assay for measuring transport across the BBB using the chimeric TfR transgenic mouse is robust and can measure greater than a 10-, 20-, 30-, 40-, or 50-fold improvement in uptake of an ADBP.

In some embodiments, in addition to using imaging methods or immunoassays to detect the presence of the ADBP in the brain, methods of detecting changes of a substrate of the effector molecule can also be used to evaluate the brain uptake of the effector molecule. In one illustrative embodiment, the ADBP comprises an effector molecule that can inhibit the enzymatic activity of an enzyme in the brain. In some embodiments, the brain uptake of an ADBP, i.e., which reflects its ability of BBB transport, can be measured by assessing enzymatic activity of an enzyme that is modulated by either the ADBP or an effector molecule joined thereto.

In some embodiments, the brain uptake of candidate ADBPs is measured in the brain. Plasma can also be monitored and the pharmacokinetic profiles evaluated. Following the administration of a candidate effector molecule, an increase in the brain-to-plasma ratio as compared to a non-BBB penetrating molecule indicates that the candidate ADBP can cross the BBB.

In some cases, a non-human transgenic animal comprising a polynucleotide encoding the chimeric TfR can be crossed with a non-human transgenic animal that has been engineered to show a certain disease phenotype. In some cases, the non-human transgenic animal is a transgenic mouse that can be crossed with various mouse models, for example, an ALS mouse model, such as described in U.S. Pat. No. 8,476,485; an AD mouse model, such as described in U.S. Pat. Nos. 5,898,094 and 6,175,057; a TSPO mouse model, such as described in US Pat. Pub. No. 2016/0050895, an autism spectrum disorder (ASD) mouse model, such as described in US Pat. Pub. No. 2014/0041062. The entire content of these aforementioned patents and patent applications are hereby incorporated by reference. In some cases, the hybrid mice produced by such crosses can be used to evaluate both the distribution of an ADBP comprising an effector molecule in the brain as well as the efficacy of the ADBP or effector molecule in treating brain diseases.

Kits

In some embodiments, kits comprising a chimeric transferrin receptor polynucleotide or polypeptide, or cells that express such polypeptides, as described herein are provided. In some embodiments, the kits are for use in screening for ADBPs as described above.

In some embodiments, the kit further comprises buffers and vessels that can be used in the assay to detect the binding between the chimeric TfR polypeptide and a candidate ADBP. In some embodiments, the kit further comprises instructional materials containing directions (i.e., protocols) for the practice of the methods described herein (e.g., instructions for using the kit for administering a composition across the blood-brain barrier). While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD-ROM), and the like. Such media may include addresses to internet sites that provide such instructional materials.

EXAMPLES

The following examples are for illustrative purposes only and should not be interpreted as limitations of the claimed invention. There are a variety of alternative techniques and procedures available to those of skill in the art which would similarly permit one to successfully perform the intended invention.

Example 1

HuTfR Mouse Generation and Characterization

Methods for generating knock-in/knock-out mice have been published in the literature and are well known to those with skill in the art. In brief, C57Bl6 mice were used to generate a knock-in of the human apical TfR mouse line via pronuclear microinjection into single cell embryos, followed by embryo transfer to pseudo pregnant females. Specifically, Cas9, sgRNAs SEQ ID NOs:10-11, and a donor DNA, SEQ ID NO:4, were introduced into the embryos. The donor DNA comprised the human apical domain coding sequence that has been codon optimized for expression in mouse, SEQ ID NO:2. The apical domain coding sequence was flanked with a left (nucleotides 1-817 of SEQ ID NO:4) and right homology arm (nucleotides 1523-2329 of SEQ ID NO:4). The donor sequence was designed in this manner such that the apical domain was to be inserted after the fourth mouse exon, and was immediately flanked at the 3' end by the ninth mouse exon. A founder male from the progeny of the female that received the embryos was bred to wild-type females to generate F1 heterozygous mice. Homozygous mice were subsequently generated from breeding of F1 generation heterozygous mice.

Example 2

Generation of Tool Antibodies for Monitoring Antibody Brain Uptake

Tool antibodies targeting human TfR or human/mouse BACE1 were generated by transforming Expi293 or ExpiCHO cells with expression plasmids containing DNA encoding the heavy and light chains and using protocols familiar to those with skill in the art. Bispecific antibodies were generated using the "knobs-into-holes" technology; knob and hole half antibodies were separately expressed and then joined using published methods. Antibodies were purified first with Protein A and then by size-exclusion chromatography. The antibodies generated for these studies were as follows:

anti-TfR: human IgG1 antibody that binds to human TfR apical domain.

anti-BACE1: human IgG1 antibody that binds to human BACE1 and cross-reacts with mouse BACE1. This antibody inhibits the enzymatic activity of BACE1.

anti-TfR/BACE1: human IgG1 knobs-into-holes bispecific antibody that binds to human TfR apical domain, as well as human and mouse BACE1. The knob half-antibody has the variable domain from the anti-BACE1 antibody; the hole half-antibody has the variable domain from the anti-TfR antibody.

Example 3

Blood Analysis of $HuTfR^{APICAL+/-}$ and $HuTfR^{APICAL+/+}$ Mice

Figure 1B:
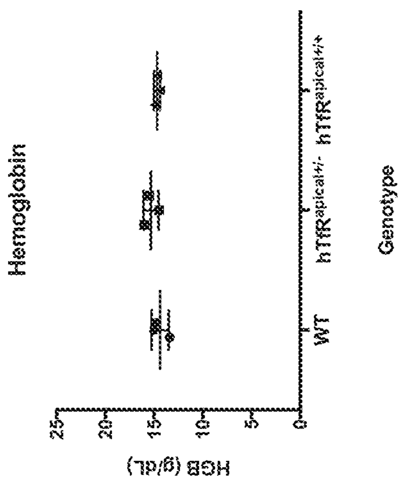
Figure 1A:
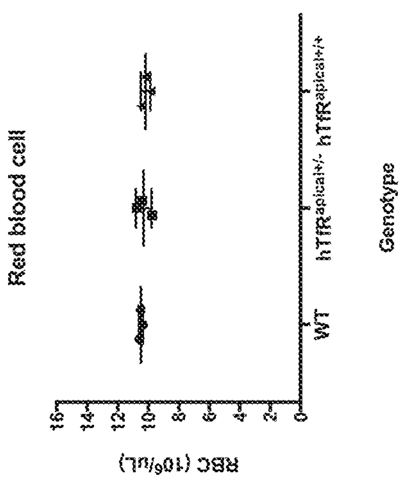

Blood was collected from wild-type C57Bl6, $huTfR^{apical+/-}$, and $huTfR^{apical-/+}$ mice (n=3/group) and a standard complete blood count (CBC) analysis was performed. No genotype-specific differences were observed in any red blood cell parameters, including total red blood cells, hemoglobin, and hematocrit levels (FIG. 1).

Example 4

Figure 2B:
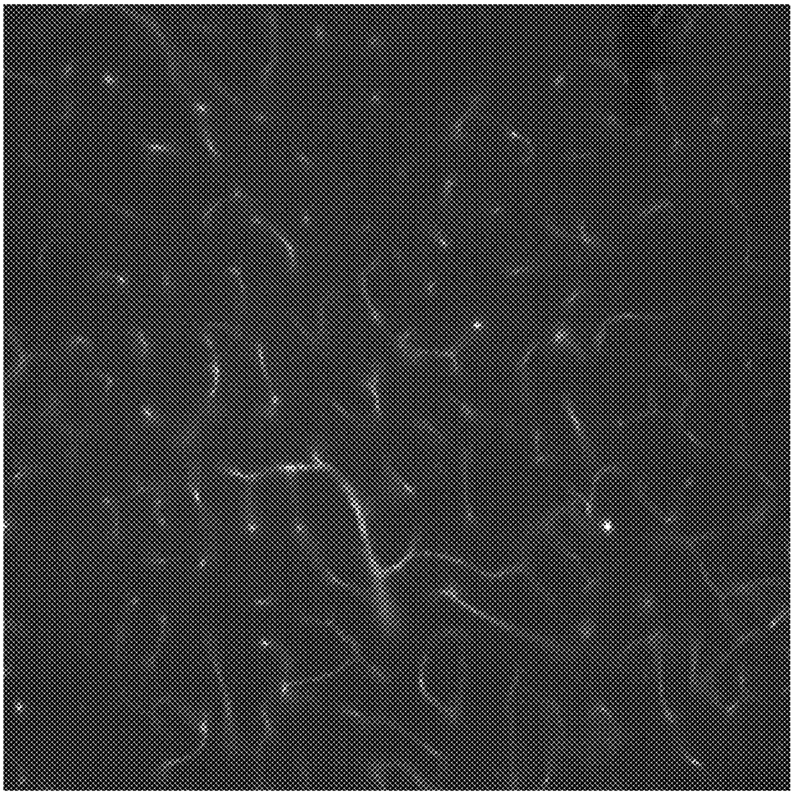
FIGS. 2A-2B show the brain vascular localization of systemically administered anti-TfR in huTfR$^{apical+/-}$ mice. 5 mg/kg of a human-apical-specific anti-TfR was intravenously administered into either C57Bl6 wild-type or chimeric huTfR$^{apical+/-}$ heterozygous mice. After one hour, mice were perfused with PBS, and brains were stained for antibody distribution. Representative images show prominent vascular localization of systemically injected anti-TfR (apical domain-specific) in the huTfR$^{apical+/-}$ heterozygous, but not in the wild-type mice. This indicates that the chimeric huTfR protein is expressed at the BBB.
Figure 2A:
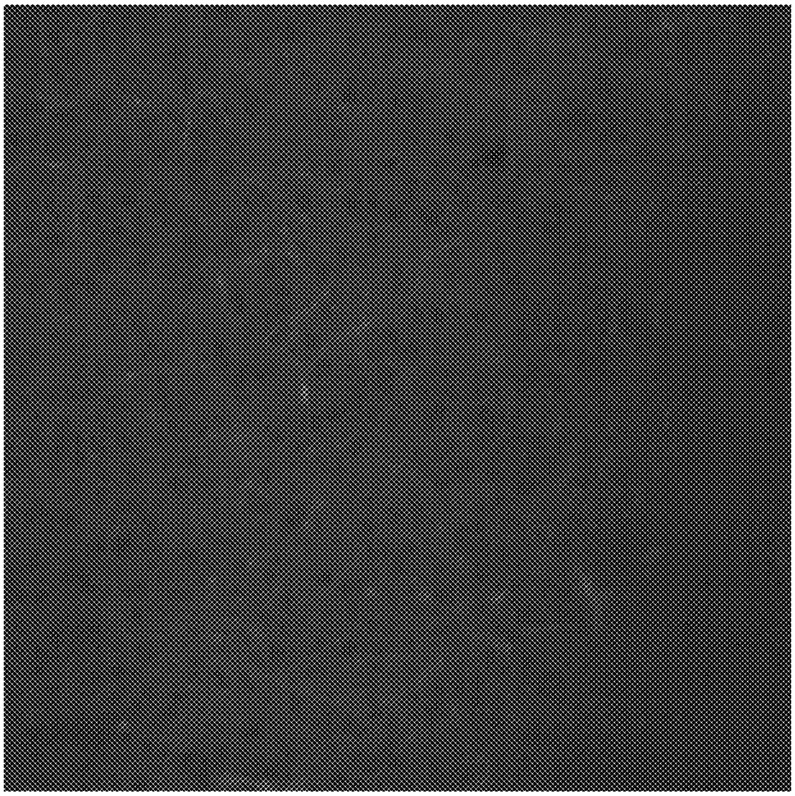

Brain Localization of TfR-Targeted Antibodies in $HuTfR^{APICAL+/-}$ and $HuTfR^{APICAL+/+}$ Mice In this example, the anti-TfR antibody was generated to evaluate brain uptake of TfR-targeted therapeutics in $huTfR^{apical+/-}$ mice. $huTfR^{apical+/-}$ mice or wild-type C57Bl6 were intravenously injected with 5 mg/kg of the anti-TfR antibody. After 1 hour, the mice were sacrificed and perfused with PBS. Hemi-brains were drop fixed in 4% PFA overnight followed by 30% sucrose preservation. Sagittal brain sections (35 μm) were cut using a microtome, blocked in 5% BSA+0.3% Triton X-100, followed by fluorescent secondary staining with Alexa488 anti-huIgG1 (1:500). Brain images were taken using a Zeiss widefield microscope with a 20× objective. Significant vascular staining was observed in the in $huTfR^{apical+/-}$ mice, indicating robust binding of human apical-specific anti-TfR on brain endothelial cells at the BBB where TfR is highly expressed (FIG. 2). In contrast, very little staining was observed in the wild-type mice.

Figure 3A:
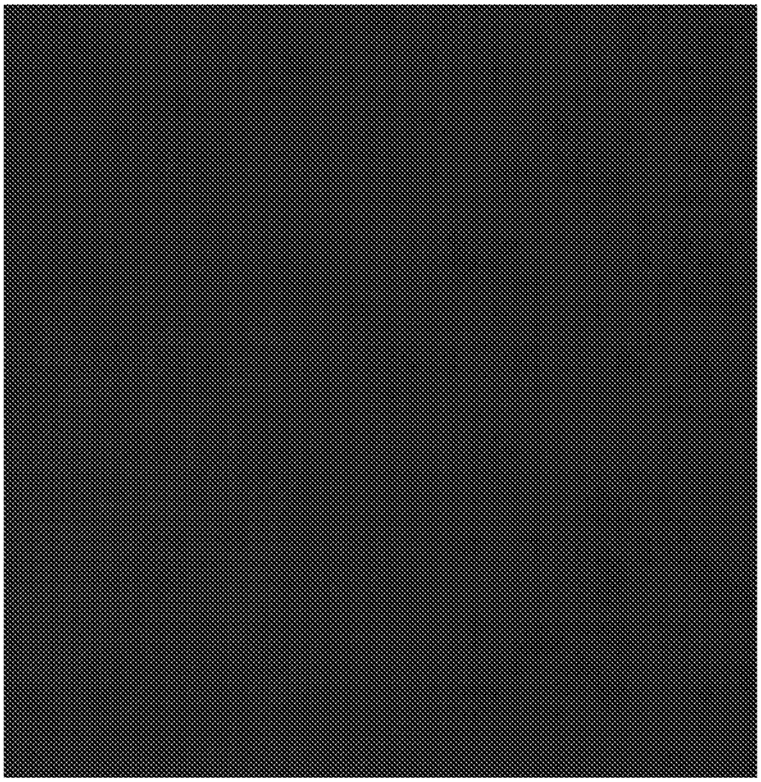
FIGS. 3A-3B show the brain parenchymal distribution of systemically administered anti-TfR/BACE1 in huTfR$^{apical+/+}$ mice. Representative images of cortical brain sections from huTfR mice show broad parenchymal distribution of intravenously-injected anti-TfR/BACE1 (50 mg/kg, 24 hrs post-dose). In contrast, no appreciable staining was observed in brain sections from huTfR$^{apical+/+}$ huTfR mice injected with anti-BACE1.
Figure 3B:
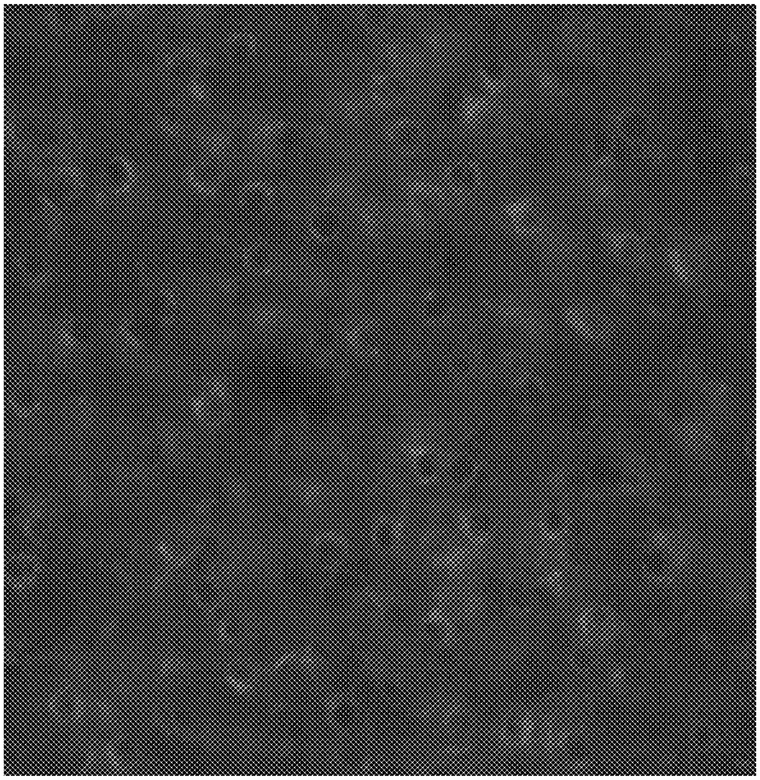

To confirm the TfR-specific BBB transport, the anti-BACE1 antibody and the anti-TfR/BACE1 bispecific antibody were tested using a similar approach as described above. $hUTfR^{apical+/+}$ mice were intravenously injected with 50 mg/kg of either antibody. After 24 hours, mice were perfused with PBS, and hemi-brains were processed and stained as described above for the $huTfR^{apical+/-}$ mice. Broad brain parenchymal staining was observed for anti-TfR/BACE1, while no staining was observed for anti-BACE1, indicating that a TfR-apical domain-binding polypeptide is required for BBB transcytosis in these mice (FIG. 3).

Example 5

Brain and Plasma PK/PD of Antibodies in $HuTfR^{APICAL+/+}$ Mice

In this example, $huTfR^{apical+/+}$ mice were intravenously injected with 50 mg/kg of either the anti-BACE1 antibody or the anti-TfR/BACE1 bispecific antibody. After 24 hours, blood was collected via cardiac puncture, and the mice were perfused with PBS. Brain tissue was homogenized in 10× tissue weight of lysis buffer containing 1% NP-40 in PBS. Blood was collected in EDTA tubes to prevent clotting and spun at 14000 rpm for 7 minutes to isolate plasma. Antibody concentrations in mouse plasma and brain lysates were quantified using a generic human IgG assay (MSD human IgG kit #K150JLD) following the manufacturer's instructions. Briefly, pre-coated plates were blocked for 30 min with MSD Blocker A. Plasma samples were diluted 1:10,000 using a Hamilton Nimbus liquid handler and added in duplicate to the blocked plates. Brain samples were homogenized in 1% NP40 lysis buffer and lysates diluted 1:10 for PK analysis. Dosing solutions were also analyzed on the same plate to confirm the correct dosage. The standard curve, 0.78-200 ng/mL IgG, was fit using a four-parameter logistic regression.

Figure 4B:
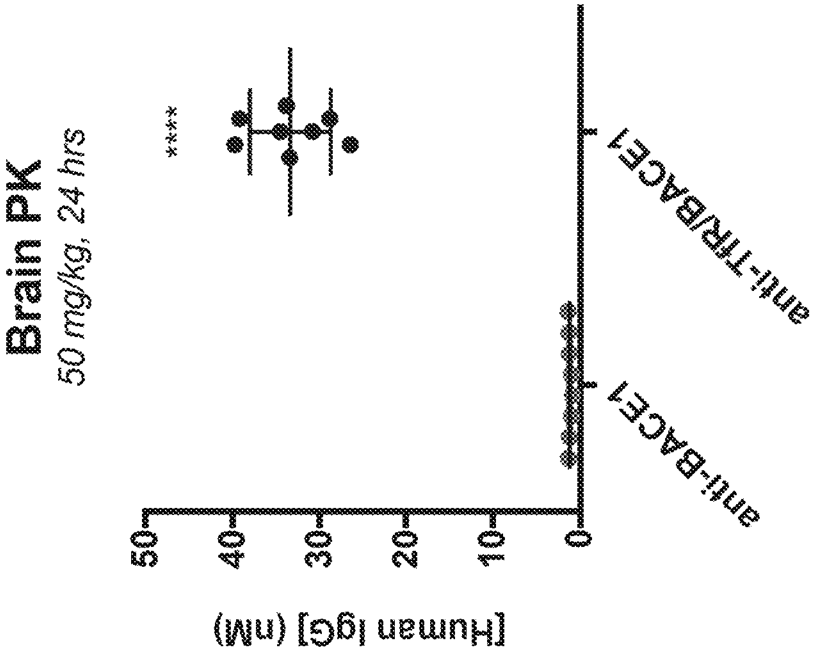
FIGS. 4A-4D show the brain uptake of an anti-TfR/BACE1 bispecific antibody and A-beta reduction followed by the administration of the bispecific antibody in huTfR$^{apical+/+}$ mice.
Figure 4A:
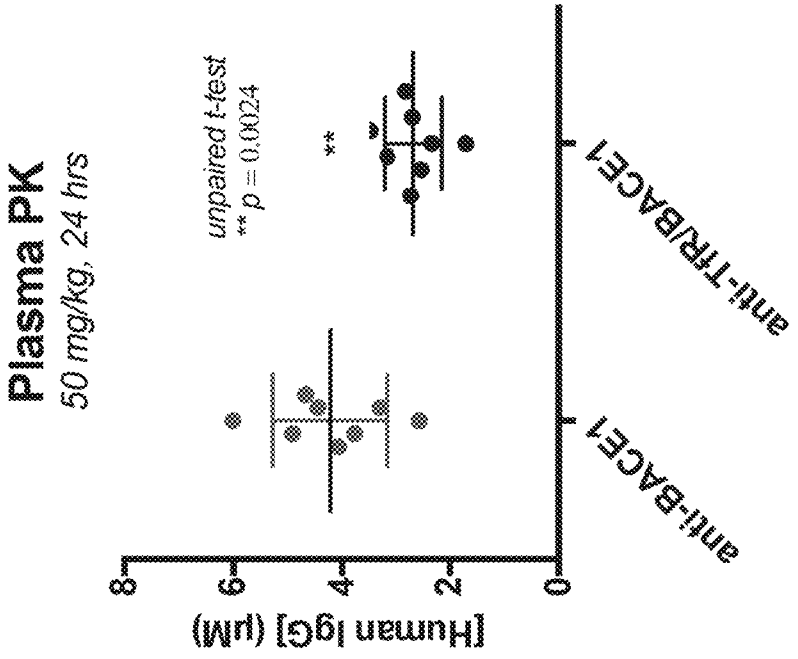

After 24 hours, the plasma levels of anti-TfR/BACE1 were lower than the levels for anti-BACE1, likely due to clearance of this antibody via binding to peripherally-expressed $huTfR^{apical}$ (FIG. 4A). In brain, a ~28-fold increase in the concentration of anti-TfR/BACE1 compared to anti-BACE1 was observed (FIG. 4B). The significant accumulation of the anti-TfR/BACE1 is due to TfR-mediated transcytosis at the BBB, this result validates the $hUTfR^{apical+/+}$ mice as a tool for measuring BBB uptake for human TfR-apical domain-binding polypeptides.

BACE1 inhibition of amyloid precursor protein (APP) cleavage was used as a pharmacodynamic readout of antibody activity in plasma and brain. Brain tissue was homogenized in 10× tissue weight of 5M guanidine-HCl and then diluted 1:10 in 0.25% casein buffer in PBS. Mouse Aβ40 levels in plasma and brain lysate were measured using a sandwich ELISA. A 384-well MaxiSorp plate was coated overnight with a polyclonal capture antibody specific for the C-terminus of the Aβ40 peptide (Millipore #ABN240). Casein-diluted guanidine brain lysates were further diluted 1:2 on the ELISA plate and added concurrently with the detection antibody, biotinylated M3.2. Plasma was analyzed at a 1:5 dilution. Samples were incubated overnight at 4° C. prior to addition of streptavidin-HRP followed by TMB substrate. The standard curve, 0.78-50 pg/mL msAβ40, was fit using a four-parameter logistic regression.

Figure 4C:
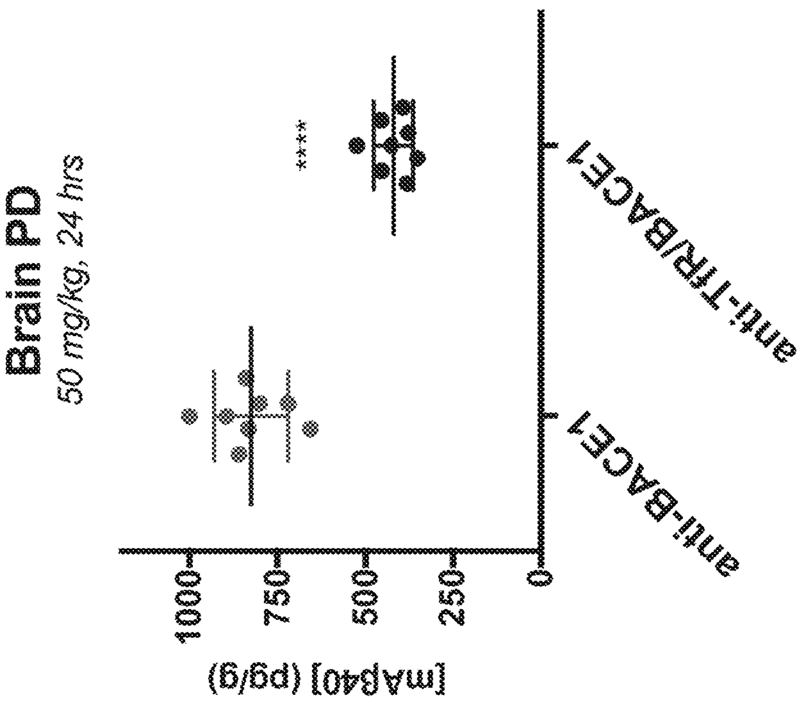
Figure 4D:
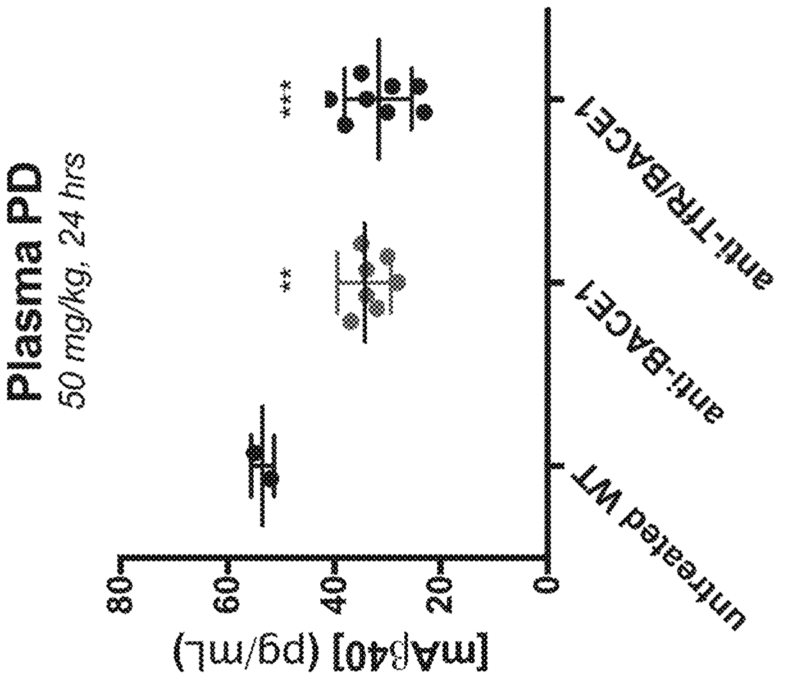

Compared to anti-BACE1, anti-TfR/BACE1 treatment resulted in an increased reduction of A-beta in $huTfR^{apical+/+}$ mice, indicating BACE1 target engagement in the brain is achieved with anti-TfR/BACE1 (FIG. 4C). Plasma A-beta was reduced to a similar extent for both anti-TfR/BACE1 and anti-BACE1, as compared to untreated wild-type mice (FIG. 4D). These data support the use of the $huTfR^{apical+/+}$ mice in target engagement studies that require human TfR-mediated brain uptake, particularly for evaluation of human TfR-apical domain-binding polypeptides.

Example 6

Expression of TfR in $HuTfR^{APICAL+/-}$ Mice

Figure 5B:
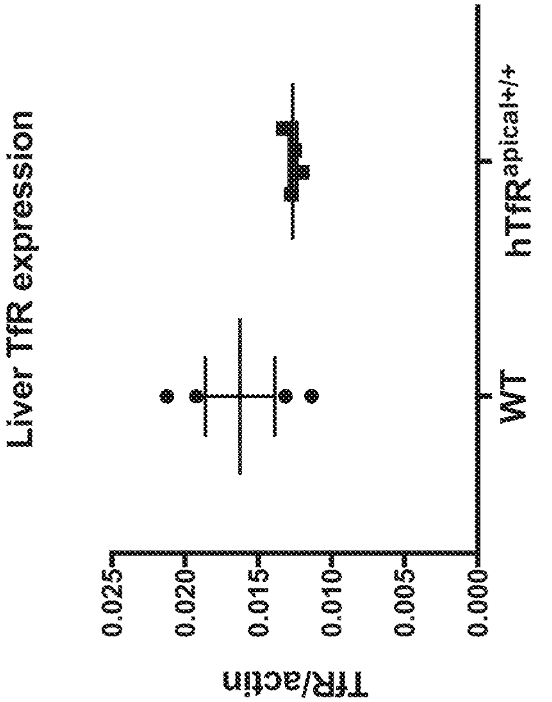
FIGS. 5A-5D show the expression of TfR in various tissues in huTfR$^{apical+/+}$ mice as compared to wild-type mice; no marked differences in total TfR expression in brain (FIG. 5A), liver (FIG. 5B), kidney (FIG. 5C), and lung (FIG. 5D) were observed. All graphs represent mean±SD, n=4-8 per group.
Figure 5A:
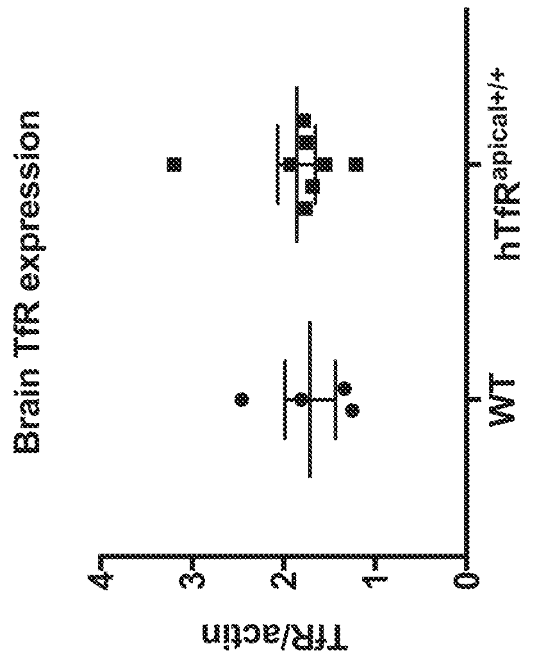
Figure 5C:
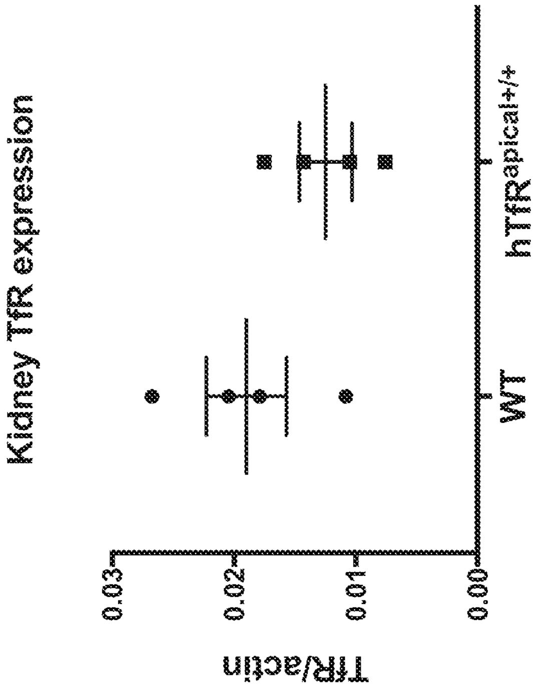
Figure 5D:
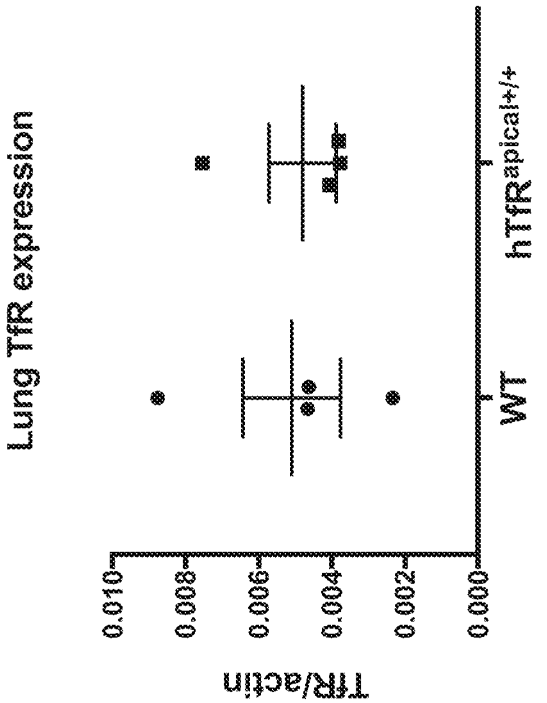

Brain and various peripheral tissues were isolated from wild-type and $huTfR^{apical+/+}$ mice in order to determine whether TfR expression levels are altered in the $huTfR^{apical+/+}$ mice. Brain, liver, lung, and kidney were taken from mice following perfusion with PBS. Tissues were homogenized in 10× tissue weight of lysis buffer containing 1% NP-40 in PBS. Samples were run on western blots and TfR expression levels were determined using a TfR antibody recognizing the intracellular portion of TfR and thus cross-reactive to both wild-type and $huTfR^{apical+/+}$ (1:2000; Thermofisher #13-6800). Quantification of TfR expression was expressed as a ratio to actin (1:5000; Abcam 8227). FIGS. 5A-5D show that TfR expression in the $huTfR^{apical+/+}$ mice is very similar to wild-type mice in brain (FIG. 5A), liver (FIG. 5B), kidney (FIG. 5C), and lung (FIG. 5D).

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

TABLE OF ILLUSTRATIVE SEQUENCES

SEQ ID NO: 1: Protein sequence of human apical domain insert
AQNSVIIVDKNGRLVYLVENPGGYVAYSKAATVTGKLVHANFGTKKDFEDLYTPVNGSIVIVRA

GKITFAEKVANAESLNAIGVLIYMDQTKFPIVNAELSFFGHAHLGTGDPYTPGFPSFNHTQFPP

SRSSGLPNIPVQTISRAAAEKLFGNMEGDCPSDWKTDSTCRMVTSESKNVKLTVSN

SEQ ID NO: 2: DNA sequence of human apical domain insert
GCTCAGAACTCCGTGATCATCGTGGATAAGAACGGCCGGCTGGTGTACCTGGTGGAGAACCCTG

GCGGATACGTGGCTTACTCTAAGGCCGCTACCGTGACAGGCAAGCTGGTGCACGCCAACTTCGG

AACCAAGAAGGACTTTGAGGATCTGTACACACCAGTGAACGGCTCTATCGTGATCGTGCGCGCT

GGAAAGATCACCTTCGCCGAGAAGGTGGCTAACGCCGAGAGCCTGAACGCCATCGGCGTGCTGA

TCTACATGGATCAGACAAAGTTTCCCATCGTGAACGCTGAGCTGTCTTTCTTTGGACACGCTCA

CCTGGGCACCGGAGACCCATACACACCCGGATTCCCTAGCTTTAACCACACCCAGTTCCCCCCT

TCCAGGTCTAGCGGACTGCCAAACATCCCCGTGCAGACAATCAGCAGAGCCGCTGCCGAGAAGC

TGTTTGGCAACATGGAGGGAGACTGCCCCTCCGATTGGAAGACCGACTCTACATGTAGGATGGT

GACCTCCGAGTCAAAAAATGTCAAACTCACCGTGTCCAAT

SEQ ID NO: 3: Chimeric TfR sequence expressed in transgenic mouse (The italicized portion represents the cytoplasmic domain, the bolded portion represents the transmembrane domain, the portion in grey represents the extracellular domain, and the bold and underlined portion represents the apical domain)
*MMDQARSAFSNLFGGEPLSYTRFSLARQVDGDNSHVEMKLAADEEENADNNMKASVRKPKRFNG*

*RLC*FAAIALVIFFLIGFMSGYLGYCKRVEQKEECVKLAETEETDKSETMETEDVPTSSRLYWAD

LKTLLSEKLNSIEFADTIKQLSQNTYTPREAGSQKDESLAYYIENQFHEFKFSKVWRDEHYVKI

QVKSSAQNSVIIVDKNGRLVYLVENPGGYVAYSKAATVTGKLVHANFGTKKDFEDLYTPVNGSI

VIVRAGKITFAEKVANAESLNAIGVLIYMDQTKFPIVNAELSFFGHAHLGTGDPYTPGFPSFNH

TQFPPSRSSGLPNIPVQTISRAAAEKLFGNMEGDCPSDWKTDSTCRMVTSESKNVKLTVSNVLK

ERRILNIFGVIKGYEEPDRYVVVGAQRDALGAGVAAKSSVGTGLLLKLAQVFSDMISKDGFRPS

RSIIFASWTAGDFGAVGATEWLEGYLSSLHLKAFTYINLDKVVLGTSNFKVSASPLLYTLMGKI

MQDVKHPVDGKSLYRDSNWISKVEKLSFDNAAYPFLAYSGIPAVSFCFCEDADYPYLGTRLDTY

EALTQKVPQLNQMVRTAAEVAGQLIIKLTHDVELNLDYEMYNSKLLSFMKDLNQFKTDIRDMGL

SLQWLYSARGDYFRATSRLTTDFHNAEKTNRFVMREINDRIMKVEYHFLSPYVSPRESPFRHIF

WGSGSHTLSALVENLKLRQKNITAFNETLFRNQLALATWTIQGVANALSGDIWNIDNEF

SEQ ID NO: 4: Sequence of full donor DNA (Left homology arm: 1-817; Right homology arm: 1523-2329; Human Apical Domain: 941-1492; Codon Optimized Sequence: 821-1522)
CTATACAGATATATAAGGATGGGGCTTTTTTTTTTTAATTTTTAAAAAAGATTTGTTTATTATT

ATATGTAAGTACACTGTAGCTGTCTTCAGACACTCCAGAAGAGGGCATCAGATCTCATTACAGA

TGGTTGTGAGCTACCATGTGGTCACTGGGATTTGAACTCAGGACCTTCAGAAGAGCAGTCAGTG

CTCTTAACTGATAAGTTAATAATAAGTTAACTGATAAGGTAATAAAGGTCCCCTATGAAAAGGG

TTCAGACCCAAAGAGTCAGAGATCCACAGGTTGAGAACCTCCTGCCCTAAATCTTGTTGCTCTC

CTTATTCAAGACCACTCCTGTTGCAGTTGCTCTTAAGCATGAGTATGCTCCCTTCTGAAAGTCT

-continued

TABLE OF ILLUSTRATIVE SEQUENCES

CCATAGCAGCCATCTCTCCAGCCCCAGAGTGAGGCTTTTAAAGGAATCTTCATGATAAATAGAA

TTTTTAAAAAAGTAACTGAAGTTACTTAAGGTGTTAAGGTACATTTTATTCCCTCAGTAACTGG

TTAATCTAGCAGTTTTGAGTCATACTTCATTTATCTTGACTTTGAAGAGTAAGATATTAAAACA

ATTTGCTTGATCCTTGAAGTAAGTATTTAAATAGACATTTTAATGCAGACTTTTTTTAGTTGAC

TGGTGGTGTTGCACGTGGTCAATCCAAGTACTCATGGGAGGCAGAGGCAGGAGGATCTCTCTCT

AGACCAGCCTGGTCTATAGAGCAAGTTCCAGGACAGCCAGGGCTACACAGAAACCTTGTTTCAA

ACAAGACTTTTATCCTTCCAGGCAGCTGAGCCAGAATACATACACTCCTAGGGAAGCTGGTTCA

CAGAAGGACGAATCCCTGGCATACTACATCGAGAATCAGTTTCACGAGTTCAAGTTTAGCAAAG

TCTGGAGAGATGAGCACTACGTGAAGATCCAGGTGAAGAGCTCCGCTCAGAACTCCGTGATCAT

CGTGGATAAGAACGGCCGGCTGGTGTACCTGGTGGAGAACCCTGGCGGATACGTGGCTTACTCT

AAGGCCGCTACCGTGACAGGCAAGCTGGTGCACGCCAACTTCGGAACCAAGAAGGACTTTGAGG

ATCTGTACACACCAGTGAACGGCTCTATCGTGATCGTGCGCGCTGGAAAGATCACCTTCGCCGA

GAAGGTGGCTAACGCCGAGAGCCTGAACGCCATCGGCGTGCTGATCTACATGGATCAGACAAAG

TTTCCCATCGTGAACGCTGAGCTGTCTTTCTTTGGACACGCTCACCTGGGCACCGGAGACCCAT

ACACACCCGGATTCCCTAGCTTTAACCACACCCAGTTCCCCCCTTCCAGGTCTAGCGGACTGCC

AAACATCCCCGTGCAGACAATCAGCAGAGCCGCTGCCGAGAAGCTGTTTGGCAACATGGAGGGA

GACTGCCCCTCCGATTGGAAGACCGACTCTACATGTAGGATGGTGACCTCCGAGTCAAAAAATG

TCAAACTCACCGTGTCCAATGTGCTGAAAGAACGACGCATCCTGAATATCTTTGGAGTTATTAA

AGGTTATGAGGAACCAGGTAAAGACCTGCTTTGTACTTTTTCACTTTACTGTTTTGCTTACTGT

AGATAGGTCTAGTGCAGGAAGGAGAAGGATGCTAGCTTGGCATGAACTGCTATATCTTGTTTGT

CCTAATGTGAACTTTGTAATATATGTGTATATAACACATAATATGGCCATGTAAGTGTATGGAG

AGGCCAGAGTTAAGTATTAAATATCTTTCTGTAATCATTTAAAATTTTACATATGAAGGTCAGT

GAACAGATTGAAGGAGTTTTGTCCAGGTGGGACTTGGATCTAAATTTTTTACAATGCCTGGCAG

CAAACACCTTTTTAATCAACTGAGCTGTCTCCCCAAATAAAGTGAATGTGATATCAGCTTGTGG

ATAATTTTTTTTTGTTGCTTTGATAAGTGGTTTTCTTACAGGATCACATACCAGTTCTGTCCAT

AGCATTAAACAAACATAACTGTCATGCAGTAGATTAATGTGCAGGGCACATCCAACAGTCACAT

TTATTAATAGGACAAAAAGTTGGACCTTATATGTAGCACACCTATAATTCCAGTGCTAGGAAGA

TCCGGGTAGGAGATCCTTAGTTCGGTGCTACTTAGTGAGGGTTTGTTTCAAAAAACAAAAGCTA

TGATGGTGTGTTGCCTTTTTTCTTTTAGACCGTTATGTTGTAGTAGGAGCCCAGAGAGACGCTT

TGGGTGCTGGTGTTGCGGCGAAGTCCAGTGTGGGAACAGGTCTTCTGTTGAAACTTGCCCAAGT

ATTCTCAGATATGATTTCAAAAGGT

SEQ ID NO: 5: Mouse TfR protein sequence (Uniprot Q62351) (The italicized portion represents the cytoplasmic domain, the bolded portion represents the transmembrane domain, the portion in grey represents the extracellular domain, and the bold and underlined portion represents the apical domain)

*MMDQARSAFSNLFGGEPLSYTRFSLARQVDGDNSHVEMKLAADEEENADNNMKASVRKPKRFNG*

*RLC*FAAIALVIFFLIGFMSGYLGYCKRVEQKEECVKLAETEETDKSETMETEDVPTSSRLYWAD

LKTLLSEKLNSIEFADTIKQLSQNTYTPREAGSQKDESLAYYIENQFHEFKFSKVWRDEHYVKI

QVKSSIGQNMVTIVQSNGNLDPVESPEGYVAFSKPTEVSGKLVHANFGTKKDFEELSYSVNGSL

-continued

TABLE OF ILLUSTRATIVE SEQUENCES

VIVRAGEITFAEKVANAQSFNAIGVLIYMDKNKFPVVEADLALFGHAHLGTGDPYTPGFPSFNH

TQFPPSQSSGLPNIPVQTISRAAAEKLFGKMEGSCPARWNIDSSCKLELSQNQNVKLIVKNVLK

ERRILNIFGVIKGYEEPDRYVVVGAQRDALGAGVAAKSSVGTGLLLKLAQVFSDMISKDGFRPS

RSIIFASWTAGDFGAVGATEWLEGYLSSLHLKAFTYINLDKVVLGTSNFKVSASPLLYTLMGKI

MQDVKHPVDGKSLYRDSNWISKVEKLSFDNAAYPFLAYSGIPAVSFCFCEDADYPYLGTRLDTY

EALTQKVPQLNQMVRTAAEVAGQLIIKLTHDVELNLDYEMYNSKLLSFMKDLNQFKTDIRDMGL

SLQWLYSARGDYFRATSRLTTDFHNAEKTNRFVMREINDRIMKVEYHFLSPYVSPRESPFRHIF

WGSGSHTLSALVENLKLRQKNITAFNETLFRNQLALATWTIQGVANALSGDIWNIDNEF

SEQ ID NO: 6: Human TfR protein sequence (Uniprot P02786) (The italicized portion represents the cytoplasmic domain, the bolded portion represents the transmembrane domain, the portion in grey represents the extracellular domain, and the bold and underlined portion represents the apical domain)
*MMDQARSAFSNLFGGEPLSYTRFSLARQVDGDNSHVEMKLAVDEEENADNNTKANVTKPKRCSG*

*SIC*YGTIAVIVFFLIGFMIGYLGYCKGVEPKTECERLAGTESPVREEPGEDFPAARRLYWDDLK

RKLSEKLDSTDFTGTIKLLNENSYVPREAGSQKDENLALYVENQFREFKLSKVWRDQHFVKIQV

KDSAQNSVIIVDKNGRLVYLVENPGGYVAYSKAATVTGKLVHANFGTKKDFEDLYTPVNGSIVI

VRAGKITFAEKVANAESLNAIGVLIYMDQTKFPIVNAELSFFGHAHLGTGDPYTPGFPSFNHTQ

FPPSRSSGLPNIPVQTISRAAAEKLFGNMEGDCPSDWKTDSTCRMVTSESKNVKLTVSNVLKEI

KILNIFGVIKGFVEPDHYVVVGAQRDAWGPGAAKSGVGTALLLKLAQMFSDMVLKDGFQPSRSI

IFASWSAGDFGSVGATEWLEGYLSSLHLKAFTYINLDKAVLGTSNFKVSASPLLYTLIEKTMQN

VKHPVTGQFLYQDSNWASKVEKLTLDNAAFPFLAYSGIPAVSFCFCEDTDYPYLGTTMDTYKEL

IERIPELNKVARAAAEVAGQFVIKLTHDVELNLDYERYNSQLLSFVRDLNQYRADIKEMGLSLQ

WLYSARGDFFRATSRLTTDFGNAEKTDRFVMKKLNDRVMRVEYHFLSPYVSPKESPFRHVFWGS

GSHTLPALLENLKLRKQNNGAFNETLFRNQLALATWTIQGAANALSGDVWDIDNEF

SEQ ID NO: 7: The apical domain of macaca mulatta (rhesus monkey) TfR (NCBI Reference Sequence NP_001244232.1); it has 95% identity to the apical domain of the native human TfR
AQNSVIIVDKNGGLVYLVENPGGYVAYSKAATVTGKLVHANFGTKKDFEDLDSPVNGSIVIVRA

GKITFAEKVANAESLNAIGVLIYMDQTKFPIVKADLSFFGHAHLGTGDPYTPGFPSFNHTQFPP

SQSSGLPNIPVQTISRAAAEKLFGNMEGDCPSDWKTDSTCKMVTSENKSVKLTVSN

SEQ ID NO: 8: The apical domain of chimpanzee TfR (NCBI Reference Sequence XP_003310238.1); it is 98% identical to the apical domain of the native human TfR
AQNSVIIVDKNGSLVYLVENPGGYVAYSKAATVTGKLVHANFGTKKDFEDLHTPVNGSIVIVRA

GKITFAEKVANAESLNAIGVLIYMDQTKFPIVNAELSFFGHAHLGTGDPYTPGFPSFNHTQFPP

SRSSGLPNIPVQTVSRAAAEKLFGNMEGDCPSDWKTDSTCRMVTSESKNVKLTVSN

SEQ ID NO: 9: The apical domain of macaca fascicularis (cynomolgous monkey) TfR (NCBI Reference Sequence XP_005545315); it is 96% identical to the apical domain of the native human TfR
AQNSVIIVDKNGGLVYLVENPGGYVAYSKAATVTGKLVHANFGTKKDFEDLDSPVNGSIVIVRA

GKITFAEKVANAESLNAIGVLIYMDQTKFPIVKADLSFFGHAHLGTGDPYTPGFPSFNHTQFPP

SQSSGLPNIPVQTISRAAAEKLFGNMEGDCPSDWKTDSTCKMVTSENKSVKLTVSN

-continued

| TABLE OF ILLUSTRATIVE SEQUENCES |
|---|
| SEQ ID NO: 10<br>GAATACATACACTCCTCGTGAGG |
| SEQ ID NO: 11<br>AGAAGAATACTTAACATCTTTGG |

What is claimed is:

1. A transgenic rodent that expresses a chimeric transferrin receptor (TfR) polypeptide at a level capable of mediating blood-brain barrier transport, wherein the transgenic rodent comprises a nucleic acid that encodes the chimeric TfR polypeptide in its genome comprising: (i) an apical domain having at least 95% identity to SEQ ID NO:1, and (ii) the transferrin binding site of the native TfR polypeptide of the rodent, wherein the chimeric TfR polypeptide is expressed in the brain of the rodent, and wherein the rodent is a mouse or rat.

2. The rodent of claim 1, wherein the apical domain comprises the amino acid sequence of SEQ ID NO: 1.

3. The rodent of claim 2, wherein the rodent is a mouse.

4. The rodent of claim 1, wherein the apical domain comprises the amino acid sequence of SEQ ID NO:7, SEQ ID NO:8, or SEQ ID NO:9.

5. The rodent of claim 1, wherein the chimeric TfR polypeptide comprises an amino acid sequence having at least 95% identity to SEQ ID NO:3.

6. The rodent of claim 1, wherein the rodent is a mouse.

7. The rodent of claim 1, wherein the rodent expresses a level of the chimeric TfR polypeptide in brain, liver, kidney, or lung tissue within 20% of the level of expression of TfR in the same tissue of a corresponding wild-type rodent of the same species.

8. The rodent of claim 1, wherein the rodent comprises a red blood cell count, level of hemoglobin, or level of hematocrit within 20% of the red blood cell count, level of hemoglobin, or level of hematocrit in a corresponding wild-type rodent of the same species.

9. The rodent of claim 1, wherein the nucleic acid sequence encoding the apical domain comprises a nucleic acid sequence having at least 95% identity to SEQ ID NO:2.

10. The rodent of claim 9, wherein the nucleic acid sequence encoding the apical domain comprises the nucleic acid sequence of SEQ ID NO:2.

11. The rodent of claim 1, wherein the rodent is homozygous for the nucleic acid encoding the chimeric TfR polypeptide.

12. The rodent of claim 1, wherein the rodent is heterozygous for the nucleic acid encoding the chimeric TfR polypeptide.

13. The rodent of claim 1, wherein the nucleic acid encoding the chimeric TfR polypeptide is expressed in one or more cells of the liver, kidney, or lung of the rodent.

14. A rodent embryonic stem (ES) cell that expresses a chimeric transferrin receptor (TfR) polypeptide at a level capable of mediating blood-brain barrier transport in a transgenic rodent generated from the ES cell, wherein the ES cell comprises a nucleic acid that encodes the chimeric TfR polypeptide in its genome comprising: (i) an apical domain having at least 95% identity to SEQ ID NO:1, and (ii) the transferrin binding site of the native TfR polypeptide of the ES cell, wherein the chimeric TfR polypeptide is expressed in the brain of the transgenic rodent generated from the ES cell, and wherein the rodent is a mouse or rat.

15. The ES cell of claim 14, wherein the apical domain comprises the amino acid sequence of SEQ ID NO: 1.

16. The ES cell of claim 15, wherein the rodent generated from the ES cell is a mouse.

17. The ES cell of claim 14, wherein the apical domain comprises the amino acid sequence of SEQ ID NO:7, SEQ ID NO:8, or SEQ ID NO:9.

18. The ES cell of claim 14, wherein the chimeric TfR polypeptide comprises an amino acid sequence having at least 95% identity to SEQ ID NO:3.

19. The ES cell of claim 14, wherein the rodent generated from the ES cell is a mouse.

20. The ES cell of claim 14, wherein the rodent generated from the ES cell expresses a level of the chimeric TfR polypeptide in brain, liver, kidney, or lung tissue within 20% of the level of expression of TfR in the same tissue of a corresponding wild-type rodent of the same species.

21. The ES cell of claim 14, wherein the rodent generated from the ES cell comprises a red blood cell count, level of hemoglobin, or level of hematocrit within 20% of the red blood cell count, level of hemoglobin, or level of hematocrit in a corresponding wild-type rodent of the same species.

22. The ES cell of claim 14, wherein the nucleic acid sequence encoding the apical domain comprises a nucleic acid sequence having at least 95% identity to SEQ ID NO:2.

23. The ES cell of claim 22, wherein the nucleic acid sequence encoding the apical domain comprises the nucleic acid sequence of SEQ ID NO:2.

24. The ES cell of claim 14, wherein the rodent generated from the ES cell is homozygous for the nucleic acid encoding the chimeric TfR polypeptide.

25. The ES cell of claim 14, wherein the rodent generated from the ES cell is heterozygous for the nucleic acid encoding the chimeric TfR polypeptide.

26. The ES cell of claim 14, wherein the nucleic acid encoding the chimeric TfR polypeptide is expressed in one or more cells of the liver, kidney, or lung of the rodent generated from the ES cell.

27. A method of screening for an apical domain binding polypeptide (ADBP) that crosses the blood-brain barrier, the method comprising:

administering an ADBP to the rodent of claim 1; and measuring the presence or an activity of the ADBP in the brain of the rodent.

28. The method of claim 27, wherein the ADBP is coupled to an effector molecule.

29. The method of claim 28, wherein the effector molecule is a small molecule, RNA, DNA, or polypeptide.

30. The method of claim 29, wherein the polypeptide is an antibody or an antigen-binding fragment thereof.

31. The method of claim 28, wherein the measuring step comprises contacting the brain or brain tissue of the rodent with an agent that binds to the effector molecule and determining the level of the effector molecule present in the brain.

32. The method of claim 28, wherein the measuring step comprises measuring a pharmacodynamic (PD) effect of the effector molecule.

* * * * *

SEQUENCE LISTING

<160> NUMBER OF SEQ ID NOS: 11

<210> SEQ ID NO 1
<211> LENGTH: 184
<212> TYPE: PRT
<213> ORGANISM: Homo sapiens

<400> SEQUENCE: 1

```
Ala Gln Asn Ser Val Ile Ile Val Asp Lys Asn Gly Arg Leu Val Tyr
1               5                   10                  15

Leu Val Glu Asn Pro Gly Gly Tyr Val Ala Tyr Ser Lys Ala Ala Thr
            20                  25                  30

Val Thr Gly Lys Leu Val His Ala Asn Phe Gly Thr Lys Lys Asp Phe
        35                  40                  45

Glu Asp Leu Tyr Thr Pro Val Asn Gly Ser Ile Val Ile Val Arg Ala
    50                  55                  60

Gly Lys Ile Thr Phe Ala Glu Lys Val Ala Asn Ala Glu Ser Leu Asn
65                  70                  75                  80

Ala Ile Gly Val Leu Ile Tyr Met Asp Gln Thr Lys Phe Pro Ile Val
                85                  90                  95

Asn Ala Glu Leu Ser Phe Phe Gly His Ala His Leu Gly Thr Gly Asp
            100                 105                 110

Pro Tyr Thr Pro Gly Phe Pro Ser Phe Asn His Thr Gln Phe Pro Pro
        115                 120                 125

Ser Arg Ser Ser Gly Leu Pro Asn Ile Pro Val Gln Thr Ile Ser Arg
    130                 135                 140

Ala Ala Ala Glu Lys Leu Phe Gly Asn Met Glu Gly Asp Cys Pro Ser
145                 150                 155                 160

Asp Trp Lys Thr Asp Ser Thr Cys Arg Met Val Thr Ser Glu Ser Lys
                165                 170                 175

Asn Val Lys Leu Thr Val Ser Asn
            180
```

<210> SEQ ID NO 2
<211> LENGTH: 552
<212> TYPE: DNA
<213> ORGANISM: Homo sapiens

<400> SEQUENCE: 2

```
gctcagaact ccgtgatcat cgtggataag aacggccggc tggtgtacct ggtggagaac     60

cctggcggat acgtggctta ctctaaggcc gctaccgtga caggcaagct ggtgcacgcc    120

aacttcggaa ccaagaagga ctttgaggat ctgtacacac cagtgaacgg ctctatcgtg    180

atcgtgcgcg ctggaaagat caccttcgcc gagaaggtgg ctaacgccga gagcctgaac    240

gccatcggcg tgctgatcta catggatcag acaaagtttc ccatcgtgaa cgctgagctg    300

tctttctttg gacacgctca cctgggcacc ggagacccat acacacccgg attccctagc    360
```

-continued

```
tttaaccaca cccagttccc cccttccagg tctagcggac tgccaaacat ccccgtgcag    420

acaatcagca gagccgctgc cgagaagctg tttggcaaca tggagggaga ctgcccctcc    480

gattggaaga ccgactctac atgtaggatg gtgacctccg agtcaaaaaa tgtcaaactc    540

accgtgtcca at                                                        552


<210> SEQ ID NO 3
<211> LENGTH: 763
<212> TYPE: PRT
<213> ORGANISM: Artificial Sequence
<220> FEATURE:
<223> OTHER INFORMATION: synthetic chimeric transferrin receptor (TfR)
      polypeptide sequence
<220> FEATURE:
<221> NAME/KEY: DOMAIN
<222> LOCATION: (1)..(67)
<223> OTHER INFORMATION: Cytoplasmic Domain
<220> FEATURE:
<221> NAME/KEY: DOMAIN
<222> LOCATION: (68)..(88)
<223> OTHER INFORMATION: Transmembrane Domain
<220> FEATURE:
<221> NAME/KEY: DOMAIN
<222> LOCATION: (89)..(763)
<223> OTHER INFORMATION: Extracellular Domain
<220> FEATURE:
<221> NAME/KEY: DOMAIN
<222> LOCATION: (198)..(381)
<223> OTHER INFORMATION: Apical Domain

<400> SEQUENCE: 3

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Ala Asp Glu Glu Glu Asn Ala
        35                  40                  45

Asp Asn Asn Met Lys Ala Ser Val Arg Lys Pro Lys Arg Phe Asn Gly
    50                  55                  60

Arg Leu Cys Phe Ala Ala Ile Ala Leu Val Ile Phe Phe Leu Ile Gly
65                  70                  75                  80

Phe Met Ser Gly Tyr Leu Gly Tyr Cys Lys Arg Val Glu Gln Lys Glu
                85                  90                  95

Glu Cys Val Lys Leu Ala Glu Thr Glu Glu Thr Asp Lys Ser Glu Thr
            100                 105                 110

Met Glu Thr Glu Asp Val Pro Thr Ser Ser Arg Leu Tyr Trp Ala Asp
        115                 120                 125

Leu Lys Thr Leu Leu Ser Glu Lys Leu Asn Ser Ile Glu Phe Ala Asp
    130                 135                 140

Thr Ile Lys Gln Leu Ser Gln Asn Thr Tyr Thr Pro Arg Glu Ala Gly
145                 150                 155                 160

Ser Gln Lys Asp Glu Ser Leu Ala Tyr Tyr Ile Glu Asn Gln Phe His
                165                 170                 175

Glu Phe Lys Phe Ser Lys Val Trp Arg Asp Glu His Tyr Val Lys Ile
            180                 185                 190

Gln Val Lys Ser Ser Ala Gln Asn Ser Val Ile Ile Val Asp Lys Asn
        195                 200                 205

Gly Arg Leu Val Tyr Leu Val Glu Asn Pro Gly Gly Tyr Val Ala Tyr
    210                 215                 220

Ser Lys Ala Ala Thr Val Thr Gly Lys Leu Val His Ala Asn Phe Gly
225                 230                 235                 240
```

-continued

```
Thr Lys Lys Asp Phe Glu Asp Leu Tyr Thr Pro Val Asn Gly Ser Ile
                245                 250                 255

Val Ile Val Arg Ala Gly Lys Ile Thr Phe Ala Glu Lys Val Ala Asn
            260                 265                 270

Ala Glu Ser Leu Asn Ala Ile Gly Val Leu Ile Tyr Met Asp Gln Thr
        275                 280                 285

Lys Phe Pro Ile Val Asn Ala Glu Leu Ser Phe Phe Gly His Ala His
    290                 295                 300

Leu Gly Thr Gly Asp Pro Tyr Thr Pro Gly Phe Pro Ser Phe Asn His
305                 310                 315                 320

Thr Gln Phe Pro Pro Ser Arg Ser Ser Gly Leu Pro Asn Ile Pro Val
                325                 330                 335

Gln Thr Ile Ser Arg Ala Ala Ala Glu Lys Leu Phe Gly Asn Met Glu
            340                 345                 350

Gly Asp Cys Pro Ser Asp Trp Lys Thr Asp Ser Thr Cys Arg Met Val
        355                 360                 365

Thr Ser Glu Ser Lys Asn Val Lys Leu Thr Val Ser Asn Val Leu Lys
    370                 375                 380

Glu Arg Arg Ile Leu Asn Ile Phe Gly Val Ile Lys Gly Tyr Glu Glu
385                 390                 395                 400

Pro Asp Arg Tyr Val Val Val Gly Ala Gln Arg Asp Ala Leu Gly Ala
                405                 410                 415

Gly Val Ala Ala Lys Ser Ser Val Gly Thr Gly Leu Leu Leu Lys Leu
            420                 425                 430

Ala Gln Val Phe Ser Asp Met Ile Ser Lys Asp Gly Phe Arg Pro Ser
        435                 440                 445

Arg Ser Ile Ile Phe Ala Ser Trp Thr Ala Gly Asp Phe Gly Ala Val
    450                 455                 460

Gly Ala Thr Glu Trp Leu Glu Gly Tyr Leu Ser Ser Leu His Leu Lys
465                 470                 475                 480

Ala Phe Thr Tyr Ile Asn Leu Asp Lys Val Val Leu Gly Thr Ser Asn
                485                 490                 495

Phe Lys Val Ser Ala Ser Pro Leu Leu Tyr Thr Leu Met Gly Lys Ile
            500                 505                 510

Met Gln Asp Val Lys His Pro Val Asp Gly Lys Ser Leu Tyr Arg Asp
        515                 520                 525

Ser Asn Trp Ile Ser Lys Val Glu Lys Leu Ser Phe Asp Asn Ala Ala
    530                 535                 540

Tyr Pro Phe Leu Ala Tyr Ser Gly Ile Pro Ala Val Ser Phe Cys Phe
545                 550                 555                 560

Cys Glu Asp Ala Asp Tyr Pro Tyr Leu Gly Thr Arg Leu Asp Thr Tyr
                565                 570                 575

Glu Ala Leu Thr Gln Lys Val Pro Gln Leu Asn Gln Met Val Arg Thr
            580                 585                 590

Ala Ala Glu Val Ala Gly Gln Leu Ile Ile Lys Leu Thr His Asp Val
        595                 600                 605

Glu Leu Asn Leu Asp Tyr Glu Met Tyr Asn Ser Lys Leu Leu Ser Phe
    610                 615                 620

Met Lys Asp Leu Asn Gln Phe Lys Thr Asp Ile Arg Asp Met Gly Leu
625                 630                 635                 640

Ser Leu Gln Trp Leu Tyr Ser Ala Arg Gly Asp Tyr Phe Arg Ala Thr
                645                 650                 655
```

```
Ser Arg Leu Thr Thr Asp Phe His Asn Ala Glu Lys Thr Asn Arg Phe
            660                 665                 670

Val Met Arg Glu Ile Asn Asp Arg Ile Met Lys Val Glu Tyr His Phe
        675                 680                 685

Leu Ser Pro Tyr Val Ser Pro Arg Glu Ser Pro Phe Arg His Ile Phe
    690                 695                 700

Trp Gly Ser Gly Ser His Thr Leu Ser Ala Leu Val Glu Asn Leu Lys
705                 710                 715                 720

Leu Arg Gln Lys Asn Ile Thr Ala Phe Asn Glu Thr Leu Phe Arg Asn
                725                 730                 735

Gln Leu Ala Leu Ala Thr Trp Thr Ile Gln Gly Val Ala Asn Ala Leu
            740                 745                 750

Ser Gly Asp Ile Trp Asn Ile Asp Asn Glu Phe
        755                 760


<210> SEQ ID NO 4
<211> LENGTH: 2329
<212> TYPE: DNA
<213> ORGANISM: Artificial Sequence
<220> FEATURE:
<223> OTHER INFORMATION: synthetic donor DNA sequence
<220> FEATURE:
<221> NAME/KEY: misc_feature
<222> LOCATION: (1)..(817)
<223> OTHER INFORMATION: left homology arm
<220> FEATURE:
<221> NAME/KEY: misc_feature
<222> LOCATION: (821)..(1522)
<223> OTHER INFORMATION: codon-optimized sequence
<220> FEATURE:
<221> NAME/KEY: misc_feature
<222> LOCATION: (941)..(1492)
<223> OTHER INFORMATION: human apical domain
<220> FEATURE:
<221> NAME/KEY: misc_feature
<222> LOCATION: (1523)..(2329)
<223> OTHER INFORMATION: righ homology arm

<400> SEQUENCE: 4

ctatacagat atataaggat ggggcttttt ttttttaatt tttaaaaaag atttgtttat     60

tattatatgt aagtacactg tagctgtctt cagacactcc agaagagggc atcagatctc    120

attacagatg gttgtgagct accatgtggt cactgggatt tgaactcagg accttcagaa    180

gagcagtcag tgctcttaac tgataagtta ataataagtt aactgataag gtaataaagg    240

tcccctatga aaagggttca gacccaaaga gtcagagatc cacaggttga gaacctcctg    300

ccctaaatct tgttgctctc cttattcaag accactcctg ttgcagttgc tcttaagcat    360

gagtatgctc ccttctgaaa gtctccatag cagccatctc tccagcccca gagtgaggct    420

tttaaaggaa tcttcatgat aaatagaatt tttaaaaaag taactgaagt tacttaaggt    480

gttaaggtac attttattcc ctcagtaact ggttaatcta gcagttttga gtcatacttc    540

atttatcttg actttgaaga gtaagatatt aaaacaattt gcttgatcct tgaagtaagt    600

atttaaatag acattttaat gcagactttt tttagttgac tggtggtgtt gcacgtggtc    660

aatccaagta ctcatgggag gcagaggcag gaggatctct ctctagacca gcctggtcta    720

tagagcaagt tccaggacag ccagggctac acagaaacct tgtttcaaac aagactttta    780

tccttccagg cagctgagcc agaatacata cactcctagg gaagctggtt cacagaagga    840

cgaatccctg gcatactaca tcgagaatca gtttcacgag ttcaagttta gcaaagtctg    900

gagagatgag cactacgtga agatccaggt gaagagctcc gctcagaact ccgtgatcat    960
```

-continued

```
cgtggataag aacggccggc tggtgtacct ggtggagaac cctggcggat acgtggctta   1020

ctctaaggcc gctaccgtga caggcaagct ggtgcacgcc aacttcggaa ccaagaagga   1080

ctttgaggat ctgtacacac cagtgaacgg ctctatcgtg atcgtgcgcg ctggaaagat   1140

caccttcgcc gagaaggtgg ctaacgccga gagcctgaac gccatcggcg tgctgatcta   1200

catggatcag acaaagtttc ccatcgtgaa cgctgagctg tctttctttg gacacgctca   1260

cctgggcacc ggagacccat acacacccgg attccctagc tttaaccaca cccagttccc   1320

cccttccagg tctagcggac tgccaaacat ccccgtgcag acaatcagca gagccgctgc   1380

cgagaagctg tttggcaaca tggagggaga ctgcccctcc gattggaaga ccgactctac   1440

atgtaggatg gtgacctccg agtcaaaaaa tgtcaaactc accgtgtcca atgtgctgaa   1500

agaacgacgc atcctgaata tctttggagt tattaaaggt tatgaggaac caggtaaaga   1560

cctgctttgt actttttcac tttactgttt tgcttactgt agataggtct agtgcaggaa   1620

ggagaaggat gctagcttgg catgaactgc tatatcttgt ttgtcctaat gtgaactttg   1680

taatatatgt gtatataaca cataatatgg ccatgtaagt gtatggagag gccagagtta   1740

agtattaaat atctttctgt aatcatttaa aattttacat atgaaggtca gtgaacagat   1800

tgaaggagtt ttgtccaggt gggacttgga tctaaatttt ttacaatgcc tggcagcaaa   1860

cacctttttta atcaactgag ctgtctcccc aaataaagtg aatgtgatat cagcttgtgg   1920

ataatttttt tttgttgctt tgataagtgg ttttcttaca ggatcacata ccagttctgt   1980

ccatagcatt aaacaaacat aactgtcatg cagtagatta atgtgcaggg cacatccaac   2040

agtcacattt attaatagga caaaaagttg gaccttatat gtagcacacc tataattcca   2100

gtgctaggaa gatccgggta ggagatcctt agttcggtgc tacttagtga gggtttgttt   2160

caaaaaacaa aagctatgat ggtgtgttgc cttttttctt ttagaccgtt atgttgtagt   2220

aggagcccag agagacgctt tgggtgctgg tgttgcggcg aagtccagtg tgggaacagg   2280

tcttctgttg aaacttgccc aagtattctc agatatgatt tcaaaaggt               2329
```

```
<210> SEQ ID NO 5
<211> LENGTH: 763
<212> TYPE: PRT
<213> ORGANISM: Mus musculus
<220> FEATURE:
<221> NAME/KEY: DOMAIN
<222> LOCATION: (1)..(67)
<223> OTHER INFORMATION: cytoplasmic domain
<220> FEATURE:
<221> NAME/KEY: DOMAIN
<222> LOCATION: (68)..(88)
<223> OTHER INFORMATION: transmembrane domain
<220> FEATURE:
<221> NAME/KEY: DOMAIN
<222> LOCATION: (89)..(763)
<223> OTHER INFORMATION: extracellular domain
<220> FEATURE:
<221> NAME/KEY: DOMAIN
<222> LOCATION: (199)..(381)
<223> OTHER INFORMATION: apical domain

<400> SEQUENCE: 5

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Ala Asp Glu Glu Glu Asn Ala
        35                  40                  45
```

-continued

```
Asp Asn Asn Met Lys Ala Ser Val Arg Lys Pro Lys Arg Phe Asn Gly
    50                  55                  60

Arg Leu Cys Phe Ala Ala Ile Ala Leu Val Ile Phe Phe Leu Ile Gly
65                  70                  75                  80

Phe Met Ser Gly Tyr Leu Gly Tyr Cys Lys Arg Val Glu Gln Lys Glu
                85                  90                  95

Glu Cys Val Lys Leu Ala Glu Thr Glu Glu Thr Asp Lys Ser Glu Thr
            100                 105                 110

Met Glu Thr Glu Asp Val Pro Thr Ser Ser Arg Leu Tyr Trp Ala Asp
        115                 120                 125

Leu Lys Thr Leu Leu Ser Glu Lys Leu Asn Ser Ile Glu Phe Ala Asp
    130                 135                 140

Thr Ile Lys Gln Leu Ser Gln Asn Thr Tyr Thr Pro Arg Glu Ala Gly
145                 150                 155                 160

Ser Gln Lys Asp Glu Ser Leu Ala Tyr Tyr Ile Glu Asn Gln Phe His
                165                 170                 175

Glu Phe Lys Phe Ser Lys Val Trp Arg Asp Glu His Tyr Val Lys Ile
            180                 185                 190

Gln Val Lys Ser Ser Ile Gly Gln Asn Met Val Thr Ile Val Gln Ser
        195                 200                 205

Asn Gly Asn Leu Asp Pro Val Glu Ser Pro Glu Gly Tyr Val Ala Phe
    210                 215                 220

Ser Lys Pro Thr Glu Val Ser Gly Lys Leu Val His Ala Asn Phe Gly
225                 230                 235                 240

Thr Lys Lys Asp Phe Glu Glu Leu Ser Tyr Ser Val Asn Gly Ser Leu
                245                 250                 255

Val Ile Val Arg Ala Gly Glu Ile Thr Phe Ala Glu Lys Val Ala Asn
            260                 265                 270

Ala Gln Ser Phe Asn Ala Ile Gly Val Leu Ile Tyr Met Asp Lys Asn
        275                 280                 285

Lys Phe Pro Val Val Glu Ala Asp Leu Ala Leu Phe Gly His Ala His
    290                 295                 300

Leu Gly Thr Gly Asp Pro Tyr Thr Pro Gly Phe Pro Ser Phe Asn His
305                 310                 315                 320

Thr Gln Phe Pro Pro Ser Gln Ser Ser Gly Leu Pro Asn Ile Pro Val
                325                 330                 335

Gln Thr Ile Ser Arg Ala Ala Ala Glu Lys Leu Phe Gly Lys Met Glu
            340                 345                 350

Gly Ser Cys Pro Ala Arg Trp Asn Ile Asp Ser Ser Cys Lys Leu Glu
        355                 360                 365

Leu Ser Gln Asn Gln Asn Val Lys Leu Ile Val Lys Asn Val Leu Lys
    370                 375                 380

Glu Arg Arg Ile Leu Asn Ile Phe Gly Val Ile Lys Gly Tyr Glu Glu
385                 390                 395                 400

Pro Asp Arg Tyr Val Val Val Gly Ala Gln Arg Asp Ala Leu Gly Ala
                405                 410                 415

Gly Val Ala Ala Lys Ser Ser Val Gly Thr Gly Leu Leu Leu Lys Leu
            420                 425                 430

Ala Gln Val Phe Ser Asp Met Ile Ser Lys Asp Gly Phe Arg Pro Ser
        435                 440                 445

Arg Ser Ile Ile Phe Ala Ser Trp Thr Ala Gly Asp Phe Gly Ala Val
    450                 455                 460

Gly Ala Thr Glu Trp Leu Glu Gly Tyr Leu Ser Ser Leu His Leu Lys
```

-continued

```
465                 470                 475                 480

Ala Phe Thr Tyr Ile Asn Leu Asp Lys Val Val Leu Gly Thr Ser Asn
                485                 490                 495

Phe Lys Val Ser Ala Ser Pro Leu Leu Tyr Thr Leu Met Gly Lys Ile
            500                 505                 510

Met Gln Asp Val Lys His Pro Val Asp Gly Lys Ser Leu Tyr Arg Asp
        515                 520                 525

Ser Asn Trp Ile Ser Lys Val Glu Lys Leu Ser Phe Asp Asn Ala Ala
    530                 535                 540

Tyr Pro Phe Leu Ala Tyr Ser Gly Ile Pro Ala Val Ser Phe Cys Phe
545                 550                 555                 560

Cys Glu Asp Ala Asp Tyr Pro Tyr Leu Gly Thr Arg Leu Asp Thr Tyr
                565                 570                 575

Glu Ala Leu Thr Gln Lys Val Pro Gln Leu Asn Gln Met Val Arg Thr
            580                 585                 590

Ala Ala Glu Val Ala Gly Gln Leu Ile Ile Lys Leu Thr His Asp Val
        595                 600                 605

Glu Leu Asn Leu Asp Tyr Glu Met Tyr Asn Ser Lys Leu Leu Ser Phe
    610                 615                 620

Met Lys Asp Leu Asn Gln Phe Lys Thr Asp Ile Arg Asp Met Gly Leu
625                 630                 635                 640

Ser Leu Gln Trp Leu Tyr Ser Ala Arg Gly Asp Tyr Phe Arg Ala Thr
                645                 650                 655

Ser Arg Leu Thr Thr Asp Phe His Asn Ala Glu Lys Thr Asn Arg Phe
            660                 665                 670

Val Met Arg Glu Ile Asn Asp Arg Ile Met Lys Val Glu Tyr His Phe
        675                 680                 685

Leu Ser Pro Tyr Val Ser Pro Arg Glu Ser Pro Phe Arg His Ile Phe
    690                 695                 700

Trp Gly Ser Gly Ser His Thr Leu Ser Ala Leu Val Glu Asn Leu Lys
705                 710                 715                 720

Leu Arg Gln Lys Asn Ile Thr Ala Phe Asn Glu Thr Leu Phe Arg Asn
                725                 730                 735

Gln Leu Ala Leu Ala Thr Trp Thr Ile Gln Gly Val Ala Asn Ala Leu
            740                 745                 750

Ser Gly Asp Ile Trp Asn Ile Asp Asn Glu Phe
        755                 760


<210> SEQ ID NO 6
<211> LENGTH: 760
<212> TYPE: PRT
<213> ORGANISM: Homo sapiens
<220> FEATURE:
<221> NAME/KEY: DOMAIN
<222> LOCATION: (1)..(67)
<223> OTHER INFORMATION: cytoplasmic domain
<220> FEATURE:
<221> NAME/KEY: DOMAIN
<222> LOCATION: (68)..(89)
<223> OTHER INFORMATION: transmembrane domain
<220> FEATURE:
<221> NAME/KEY: DOMAIN
<222> LOCATION: (90)..(760)
<223> OTHER INFORMATION: extracellular domain
<220> FEATURE:
<221> NAME/KEY: DOMAIN
<222> LOCATION: (196)..(379)
<223> OTHER INFORMATION: apical domain

<400> SEQUENCE: 6
```

-continued

```
Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
        355                 360                 365

Glu Ser Lys Asn Val Lys Leu Thr Val Ser Asn Val Leu Lys Glu Ile
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415
```

-continued

```
Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760
```

<210> SEQ ID NO 7
<211> LENGTH: 184
<212> TYPE: PRT
<213> ORGANISM: Macaca mulatta

<400> SEQUENCE: 7

```
Ala Gln Asn Ser Val Ile Ile Val Asp Lys Asn Gly Gly Leu Val Tyr
1               5                   10                  15

Leu Val Glu Asn Pro Gly Gly Tyr Val Ala Tyr Ser Lys Ala Ala Thr
            20                  25                  30
```

Val Thr Gly Lys Leu Val His Ala Asn Phe Gly Thr Lys Lys Asp Phe
35 40 45

Glu Asp Leu Asp Ser Pro Val Asn Gly Ser Ile Val Ile Val Arg Ala
50 55 60

Gly Lys Ile Thr Phe Ala Glu Lys Val Ala Asn Ala Glu Ser Leu Asn
65 70 75 80

Ala Ile Gly Val Leu Ile Tyr Met Asp Gln Thr Lys Phe Pro Ile Val
85 90 95

Lys Ala Asp Leu Ser Phe Phe Gly His Ala His Leu Gly Thr Gly Asp
100 105 110

Pro Tyr Thr Pro Gly Phe Pro Ser Phe Asn His Thr Gln Phe Pro Pro
115 120 125

Ser Gln Ser Ser Gly Leu Pro Asn Ile Pro Val Gln Thr Ile Ser Arg
130 135 140

Ala Ala Ala Glu Lys Leu Phe Gly Asn Met Glu Gly Asp Cys Pro Ser
145 150 155 160

Asp Trp Lys Thr Asp Ser Thr Cys Lys Met Val Thr Ser Glu Asn Lys
165 170 175

Ser Val Lys Leu Thr Val Ser Asn
180

<210> SEQ ID NO 8
<211> LENGTH: 184
<212> TYPE: PRT
<213> ORGANISM: Pan troglodytes

<400> SEQUENCE: 8

Ala Gln Asn Ser Val Ile Ile Val Asp Lys Asn Gly Ser Leu Val Tyr
1 5 10 15

Leu Val Glu Asn Pro Gly Gly Tyr Val Ala Tyr Ser Lys Ala Ala Thr
20 25 30

Val Thr Gly Lys Leu Val His Ala Asn Phe Gly Thr Lys Lys Asp Phe
35 40 45

Glu Asp Leu His Thr Pro Val Asn Gly Ser Ile Val Ile Val Arg Ala
50 55 60

Gly Lys Ile Thr Phe Ala Glu Lys Val Ala Asn Ala Glu Ser Leu Asn
65 70 75 80

Ala Ile Gly Val Leu Ile Tyr Met Asp Gln Thr Lys Phe Pro Ile Val
85 90 95

Asn Ala Glu Leu Ser Phe Phe Gly His Ala His Leu Gly Thr Gly Asp
100 105 110

Pro Tyr Thr Pro Gly Phe Pro Ser Phe Asn His Thr Gln Phe Pro Pro
115 120 125

Ser Arg Ser Ser Gly Leu Pro Asn Ile Pro Val Gln Thr Val Ser Arg
130 135 140

Ala Ala Ala Glu Lys Leu Phe Gly Asn Met Glu Gly Asp Cys Pro Ser
145 150 155 160

Asp Trp Lys Thr Asp Ser Thr Cys Arg Met Val Thr Ser Glu Ser Lys
165 170 175

Asn Val Lys Leu Thr Val Ser Asn
180

<210> SEQ ID NO 9
<211> LENGTH: 184
<212> TYPE: PRT

-continued

<213> ORGANISM: Macaca fascicularis

<400> SEQUENCE: 9

```
Ala Gln Asn Ser Val Ile Ile Val Asp Lys Asn Gly Gly Leu Val Tyr
1               5                   10                  15

Leu Val Glu Asn Pro Gly Gly Tyr Val Ala Tyr Ser Lys Ala Ala Thr
            20                  25                  30

Val Thr Gly Lys Leu Val His Ala Asn Phe Gly Thr Lys Lys Asp Phe
        35                  40                  45

Glu Asp Leu Asp Ser Pro Val Asn Gly Ser Ile Val Ile Val Arg Ala
    50                  55                  60

Gly Lys Ile Thr Phe Ala Glu Lys Val Ala Asn Ala Glu Ser Leu Asn
65                  70                  75                  80

Ala Ile Gly Val Leu Ile Tyr Met Asp Gln Thr Lys Phe Pro Ile Val
                85                  90                  95

Lys Ala Asp Leu Ser Phe Phe Gly His Ala His Leu Gly Thr Gly Asp
            100                 105                 110

Pro Tyr Thr Pro Gly Phe Pro Ser Phe Asn His Thr Gln Phe Pro Pro
        115                 120                 125

Ser Gln Ser Ser Gly Leu Pro Asn Ile Pro Val Gln Thr Ile Ser Arg
    130                 135                 140

Ala Ala Ala Glu Lys Leu Phe Gly Asn Met Glu Gly Asp Cys Pro Ser
145                 150                 155                 160

Asp Trp Lys Thr Asp Ser Thr Cys Lys Met Val Thr Ser Glu Asn Lys
                165                 170                 175

Ser Val Lys Leu Thr Val Ser Asn
            180
```

<210> SEQ ID NO 10
<211> LENGTH: 23
<212> TYPE: DNA
<213> ORGANISM: Artificial Sequence
<220> FEATURE:
<223> OTHER INFORMATION: synthetic sgRNA sequence

<400> SEQUENCE: 10
gaatacatac actcctcgtg agg 23

<210> SEQ ID NO 11
<211> LENGTH: 23
<212> TYPE: DNA
<213> ORGANISM: Artificial Sequence
<220> FEATURE:
<223> OTHER INFORMATION: synthetic sgRNA sequence

<400> SEQUENCE: 11
agaagaatac ttaacatctt tgg 23